(12) United States Patent
Matityahu

(10) Patent No.: US 8,142,432 B2
(45) Date of Patent: Mar. 27, 2012

(54) APPARATUS FOR REPOSITIONING PORTIONS OF FRACTURED BONE AND METHOD OF USING SAME

(75) Inventor: Amir M. Matityahu, Los Altos, CA (US)

(73) Assignee: Synthes USA, LLC, West Chester, PA (US)

( * ) Notice: Subject to any disclaimer, the term of this patent is extended or adjusted under 35 U.S.C. 154(b) by 685 days.

(21) Appl. No.: 11/773,134

(22) Filed: Jul. 3, 2007

(65) Prior Publication Data

US 2008/0188852 A1  Aug. 7, 2008

Related U.S. Application Data

(60) Provisional application No. 60/899,727, filed on Feb. 5, 2007.

(51) Int. Cl.
*A61B 17/00* (2006.01)
*A61F 4/00* (2006.01)
*A61F 5/04* (2006.01)

(52) U.S. Cl. ............................................ 606/54; 606/59

(58) Field of Classification Search .............. 606/53–54, 606/58–59, 98; 602/12
See application file for complete search history.

(56) References Cited

U.S. PATENT DOCUMENTS

| | | |
|---|---|---|
| 2,267,925 A | 2/1941 | Johnston |
| 2,699,774 A | 1/1955 | Livingston |
| 3,255,747 A | 9/1960 | Cochran et al. |
| 3,463,148 A | 8/1969 | Treace |
| 4,484,570 A | 11/1984 | Sutter et al. |
| 5,057,111 A | 10/1991 | Park |
| 5,735,853 A | 4/1998 | Olerud |
| 5,954,722 A | 9/1999 | Bono |
| 6,235,033 B1 | 5/2001 | Brace et al. |
| 6,293,949 B1 | 9/2001 | Justis et al. |
| 6,331,179 B1 | 12/2001 | Freid et al. |
| 6,342,055 B1 | 1/2002 | Eisermann et al. |
| 6,575,975 B2 | 6/2003 | Brace et al. |
| 6,663,632 B1 | 12/2003 | Frigg |
| 6,746,448 B2 * | 6/2004 | Weiner et al. .................... 606/54 |
| 6,786,909 B1 | 9/2004 | Dransfeld et al. |
| 6,890,334 B2 | 5/2005 | Brace et al. |
| 6,893,443 B2 | 5/2005 | Frigg et al. |
| 6,926,720 B2 | 8/2005 | Castaneda |
| 7,195,633 B2 | 3/2007 | Medoff et al. |
| 2002/0058939 A1 | 5/2002 | Wagner et al. |
| 2003/0105461 A1 | 6/2003 | Putnam |
| 2003/0199876 A1 | 10/2003 | Brace et al. |
| 2004/0015169 A1 | 1/2004 | Gause |

(Continued)

*Primary Examiner* — Eduardo C Robert
*Assistant Examiner* — Christina Negrelli
(74) *Attorney, Agent, or Firm* — Fay Kaplun Marcin, LLP

(57) ABSTRACT

A medical apparatus for use with an outrigger and at least one fastening pin to reposition first and second portions of a bone of a mammalian body. The apparatus includes a framework and a first fastening assembly for coupling the framework to the outrigger and thus the at least one fastening pin and the first end portion of the bone. The first end portion of an elongate pin is provided with a sharpened tip for penetrating the second portion of the bone. A second fastening assembly couples the second end portion of the elongate pin to the framework. At least one adjustment assembly is carried by at least one of the framework and the first and second fastening assemblies for moving the first end portion of the elongate pin relative to the outrigger so as to reposition the second portion of the bone relative to the first portion of the bone. A method for using the apparatus is provided.

29 Claims, 20 Drawing Sheets

U.S. PATENT DOCUMENTS

| | | |
|---|---|---|
| 2004/0059335 A1 | 3/2004 | Weaver et al. |
| 2004/0068319 A1 | 4/2004 | Cordaro |
| 2004/0127896 A1 | 7/2004 | Lombardo et al. |
| 2004/0127904 A1 | 7/2004 | Konieczynski et al. |
| 2004/0143203 A1 | 7/2004 | Weiner et al. |
| 2004/0167522 A1 | 8/2004 | Niederberger et al. |
| 2004/0181228 A1 | 9/2004 | Wagner et al. |
| 2004/0220570 A1 | 11/2004 | Frigg |
| 2004/0236332 A1 | 11/2004 | Frigg |
| 2004/0254579 A1 | 12/2004 | Buhren et al. |
| 2005/0010226 A1 | 1/2005 | Grady, Jr. et al. |
| 2005/0043736 A1 | 2/2005 | Mathieu et al. |
| 2005/0049594 A1 | 3/2005 | Wack et al. |
| 2005/0080421 A1 | 4/2005 | Weaver et al. |
| 2005/0107796 A1 | 5/2005 | Gerlach et al. |
| 2005/0149027 A1 | 7/2005 | Campbell et al. |
| 2005/0154392 A1 | 7/2005 | Medoff et al. |
| 2005/0165400 A1 | 7/2005 | Fernandez |
| 2007/0162016 A1 | 7/2007 | Matityahu |

* cited by examiner

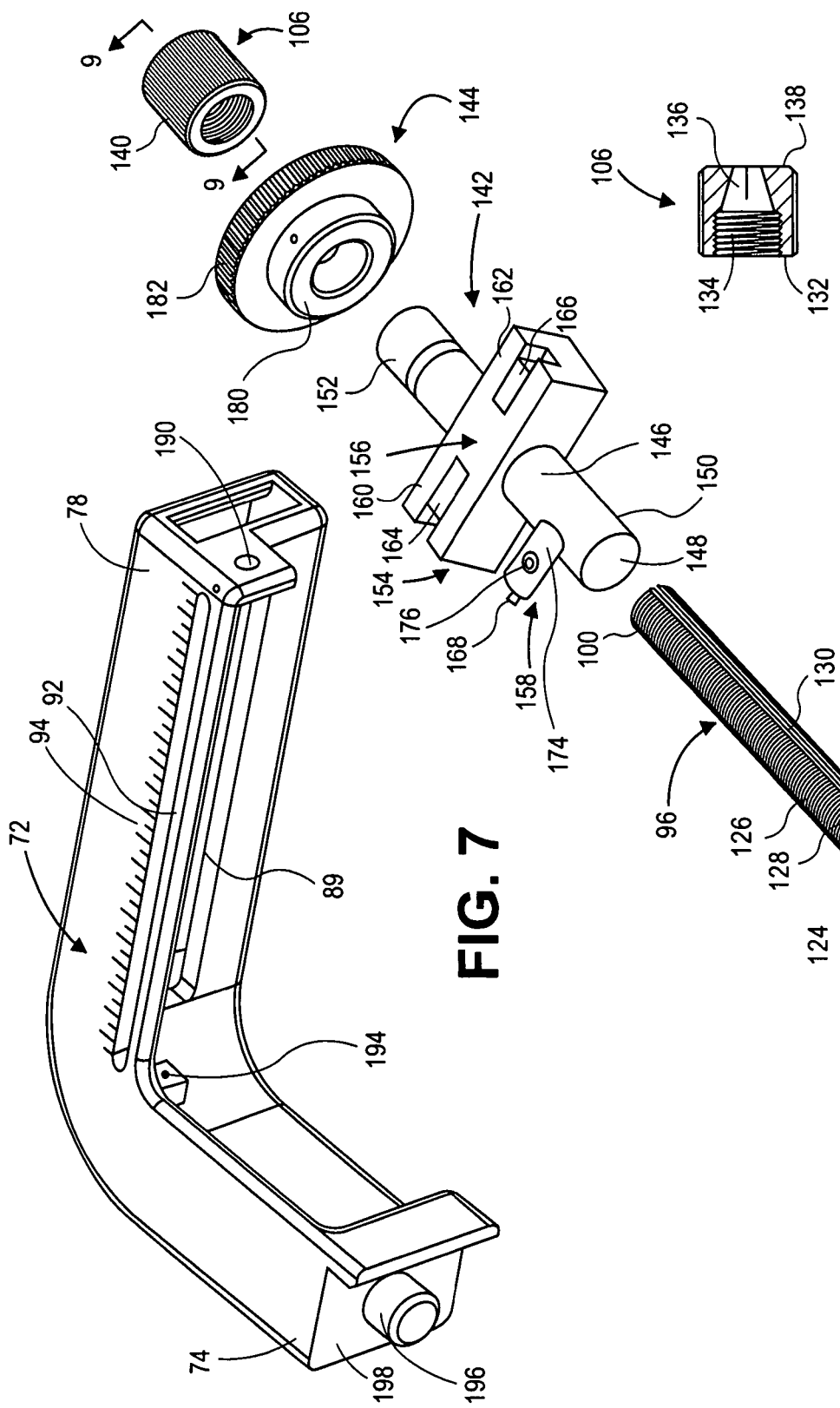

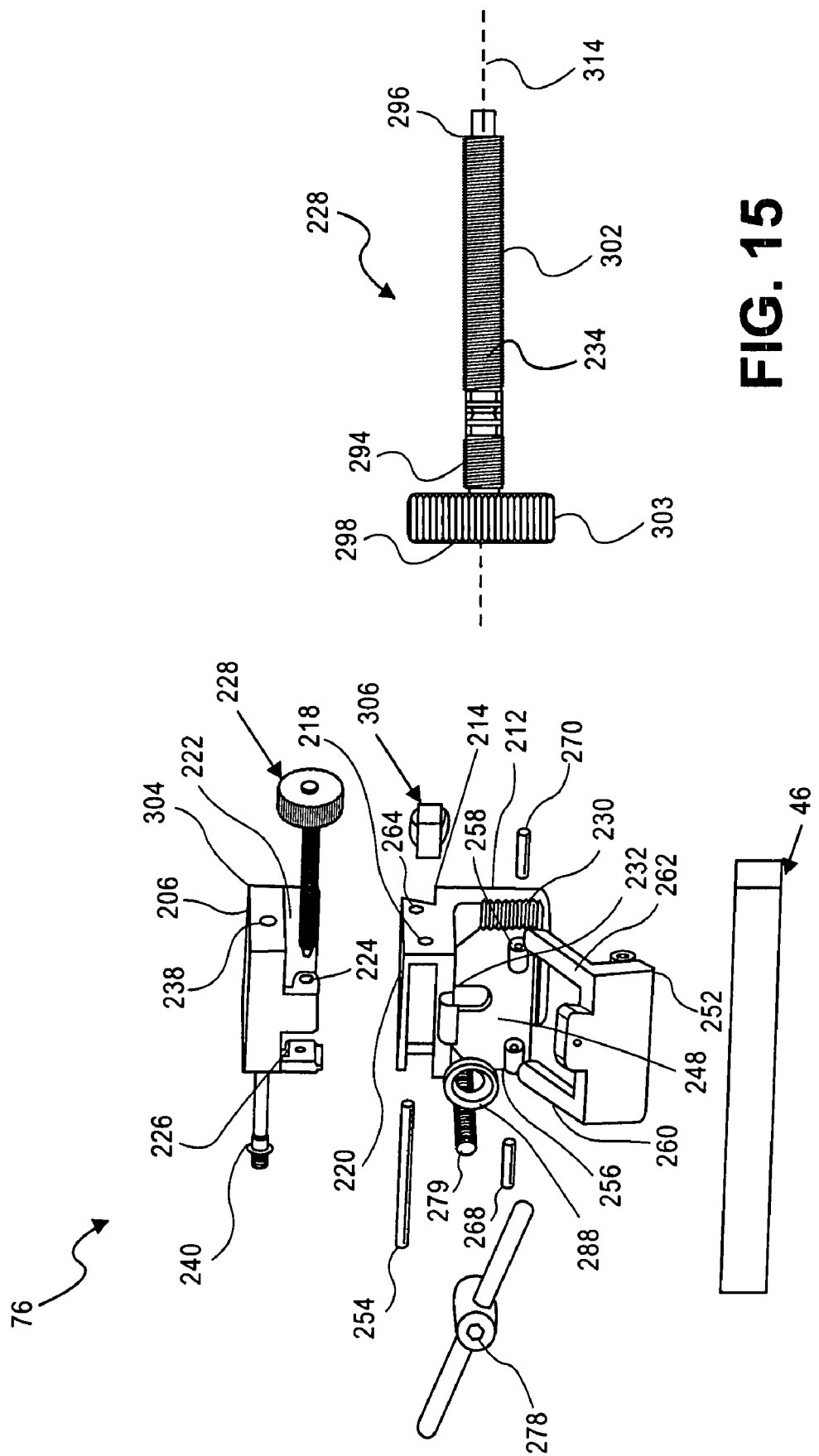

APPARATUS FOR REPOSITIONING PORTIONS OF FRACTURED BONE AND METHOD OF USING SAME

CROSS-REFERENCE TO RELATED APPLICATIONS

This application claims the benefit of related U.S. Provisional Patent Application Ser. No. 60/899,727, filed Feb. 5, 2007, which application is hereby incorporated in its entirety by reference.

SCOPE OF THE INVENTION

The present invention relates to an apparatus and method for repairing a segmented bone.

BACKGROUND

Current methods of repair of segmented bones, such as fractured or osteotomised bones in a mammalian body involve moving or reducing a portion of the bone, generally the distal portion of the bone, either by grasping the bone portion with a human hand or clamp or attaching a pin to the bone portion and grasping the pin with a hand to move the bone portion. These methods often include making an incision through the skin of the patient and then drilling into the bone, then moving the bone portion by hand into position and holding the bone portion once positioned. Other methods may include a large incision in the tissue surrounding the bone for viewing and manual alignment of the bone portion, as well as manual affixation of the separated bone portions. Unfortunately, such methods are imprecise and are often physically hard on the patient and the surgeon. Other current methods include utilization of a screw advanced through a targeting jig and bone plate into the bone portion, whereby rotation of the screw in the bone portion cause the bone portion to be drawn toward the bone plate, namely, causing the bone portion to move relative to the bone plate in a direction generally perpendicular to the plate, so as to reposition the bone portion. Unfortunately, such screws often can not move the bone to the plate due to the position of the bone or move in an oblique fashion causing the screw to bend and, on occasion, break.

What is needed in the art is an apparatus and assembly that is not highly invasive for repositioning percutaneously portions of a segmented bone to permit securement of the bone to a bone plate or other corrective device in a measured, precise, and reproducible manner.

SUMMARY OF THE INVENTION

A medical apparatus is provided for use with an outrigger and at least one fastening pin to reposition first and second portions of a bone of a mammalian body. The apparatus includes a framework and a first fastening assembly for coupling the framework to the outrigger and thus the at least one fastening pin and the first end portion of the bone. The first end portion of an elongate pin is provided with a sharpened tip for penetrating the second portion of the bone. A second fastening assembly couples the second end portion of the elongate pin to the framework. At least one adjustment assembly is carried by at least one of the framework and the first and second fastening assemblies for moving the first end portion of the elongate pin relative to the outrigger so as to reposition the second portion of the bone relative to the first portion of the bone. A method for using the apparatus is provided.

BRIEF DESCRIPTION OF THE DRAWINGS

FIG. 7 is a side perspective view of the bridge of FIG. 6, without the pin and the related fastening and adjustment assemblies, taken along the line 7-7 of FIG. 6.

FIG. 8 is an exploded side perspective view of a portion of the fastening assembly and a portion of the adjustment assemblies of FIG. 6 without the pin.

FIG. 9 is a cross-sectional view of the spindle nut of the fastening assembly of FIG. 6, taken along line 9-9 of FIG. 8.

FIG. 14 is another exploded view of the fastening assembly and adjustment assembly of FIG. 12, taken along the line 14-14 of FIG. 13.

FIG. 15 is a side elevational view of the short metering screw of the adjustment assembly of FIG. 12.

DESCRIPTION OF THE INVENTION

Figure 1:
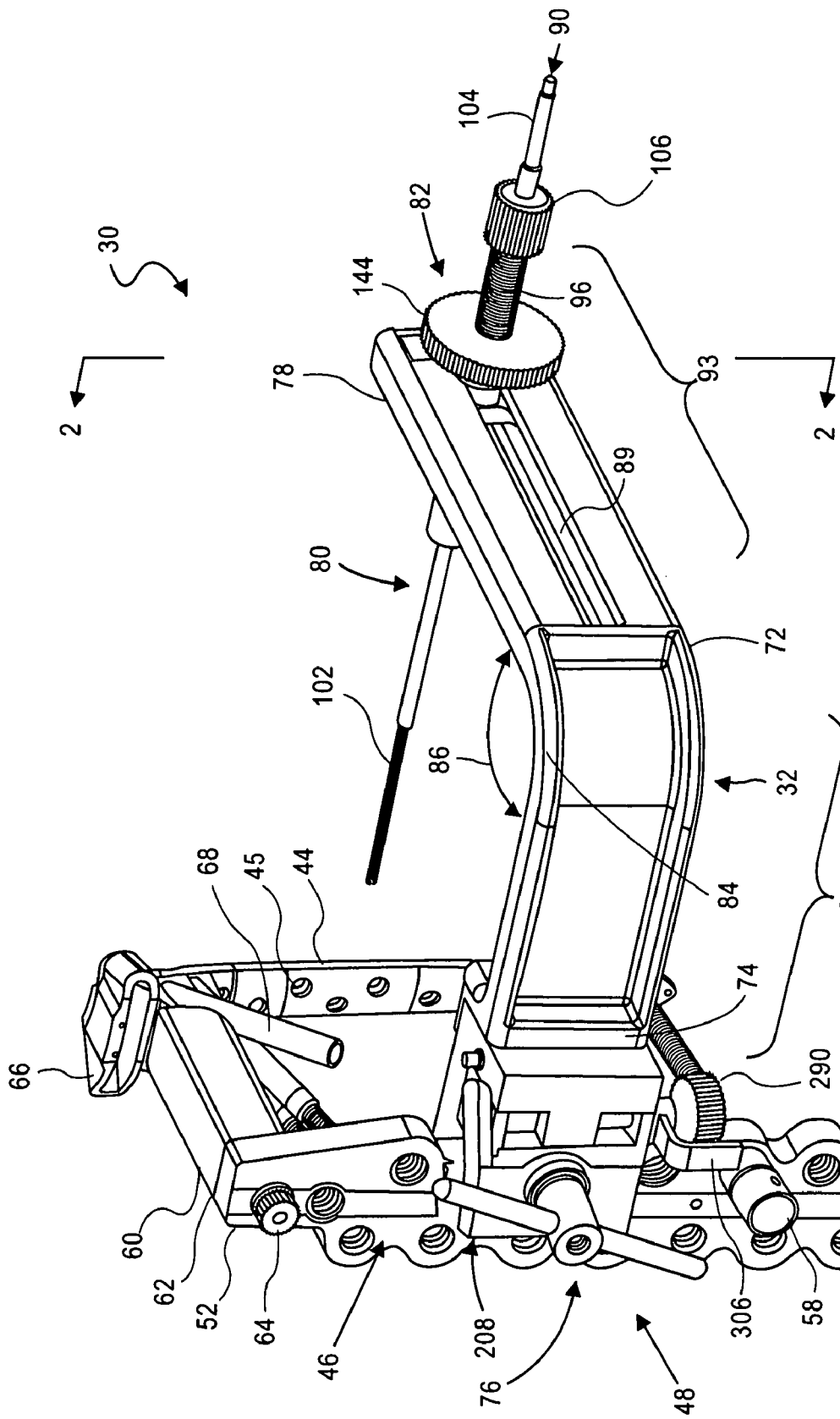
FIG. 1 is a side perspective view of the medical apparatus assembly of the present invention coupled to a targeting jig secured to a right tibia bone plate.
Figure 2:
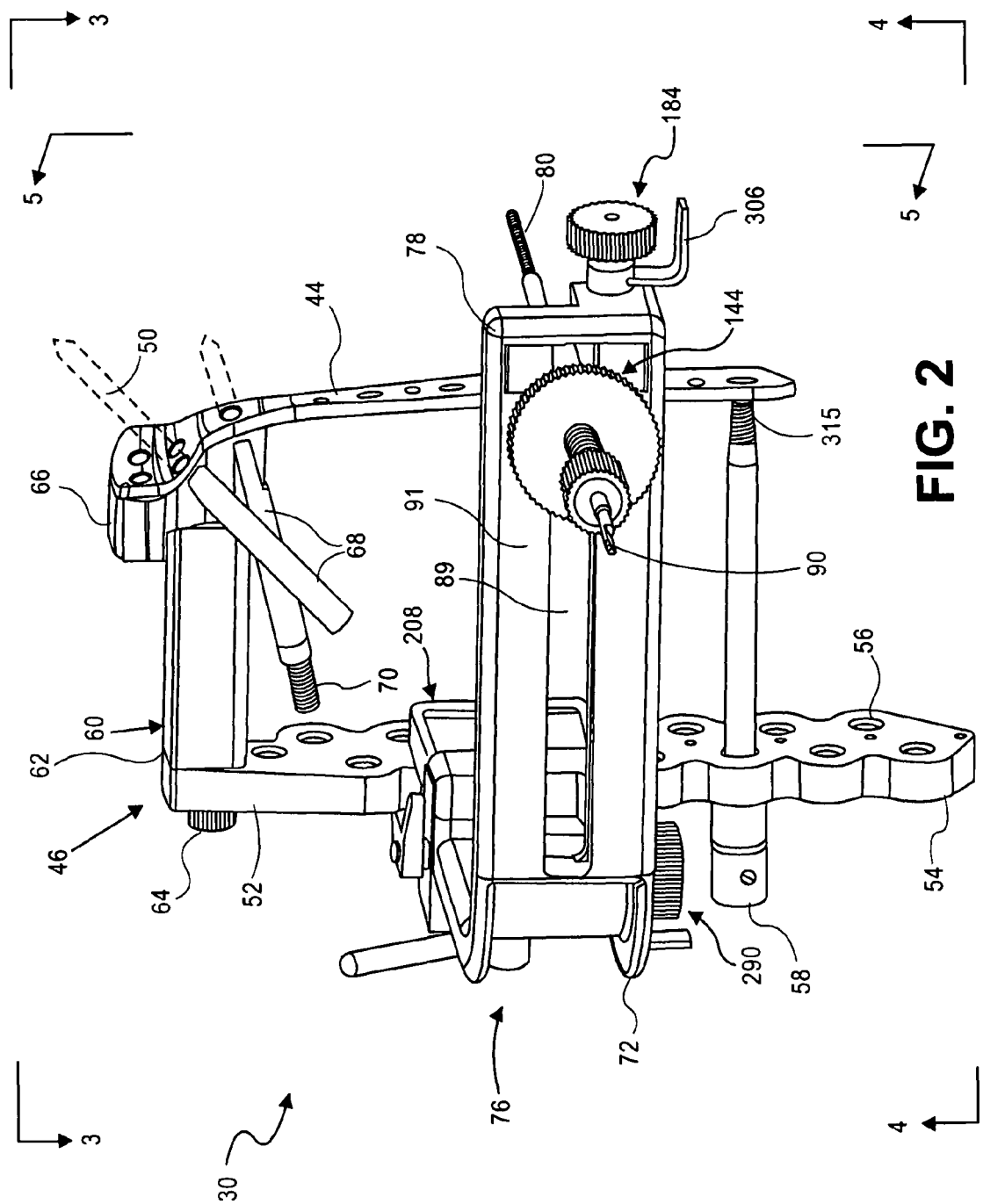
FIG. 2 is a front elevational view of the medical apparatus assembly of FIG. 1 taken along the line 2-2 of FIG. 1.
Figure 3:
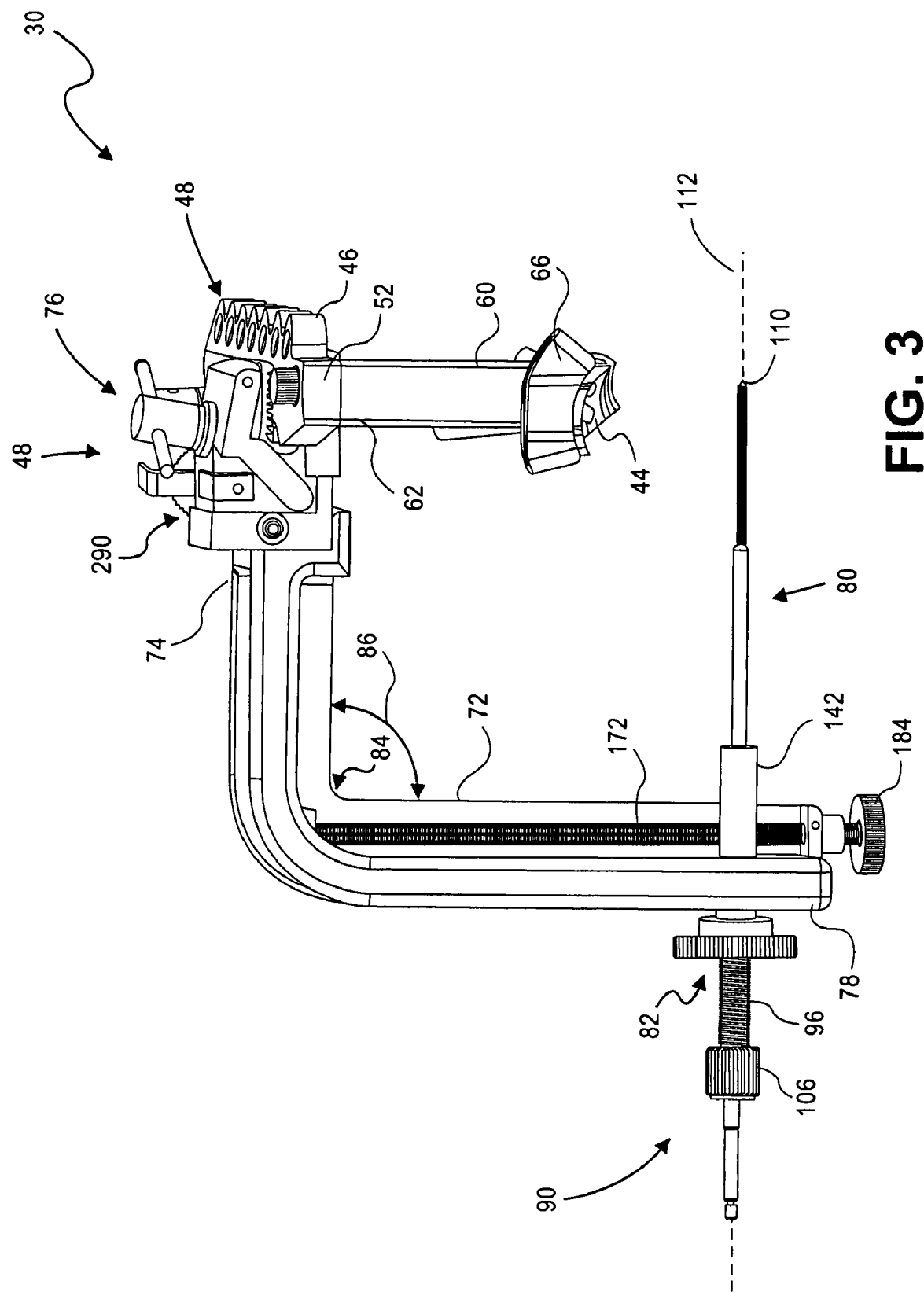
FIG. 3 is a top plan view of the medical apparatus assembly of FIG. 1 taken along the line 3-3 of FIG. 2.
Figure 4:
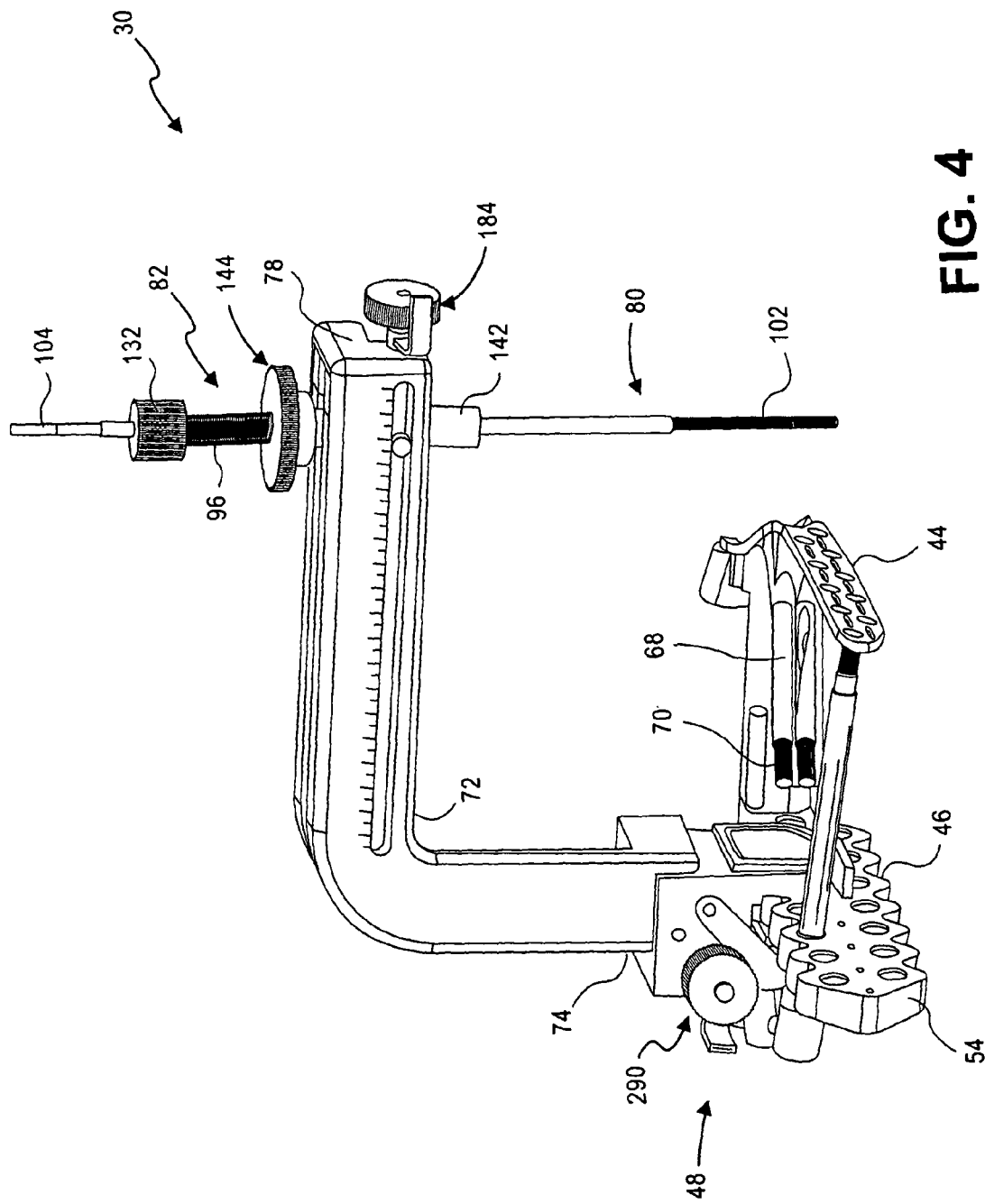
FIG. 4 is a bottom plan view of the medical apparatus assembly of FIG. 1 taken along the line 4-4 of FIG. 2.
Figure 5:
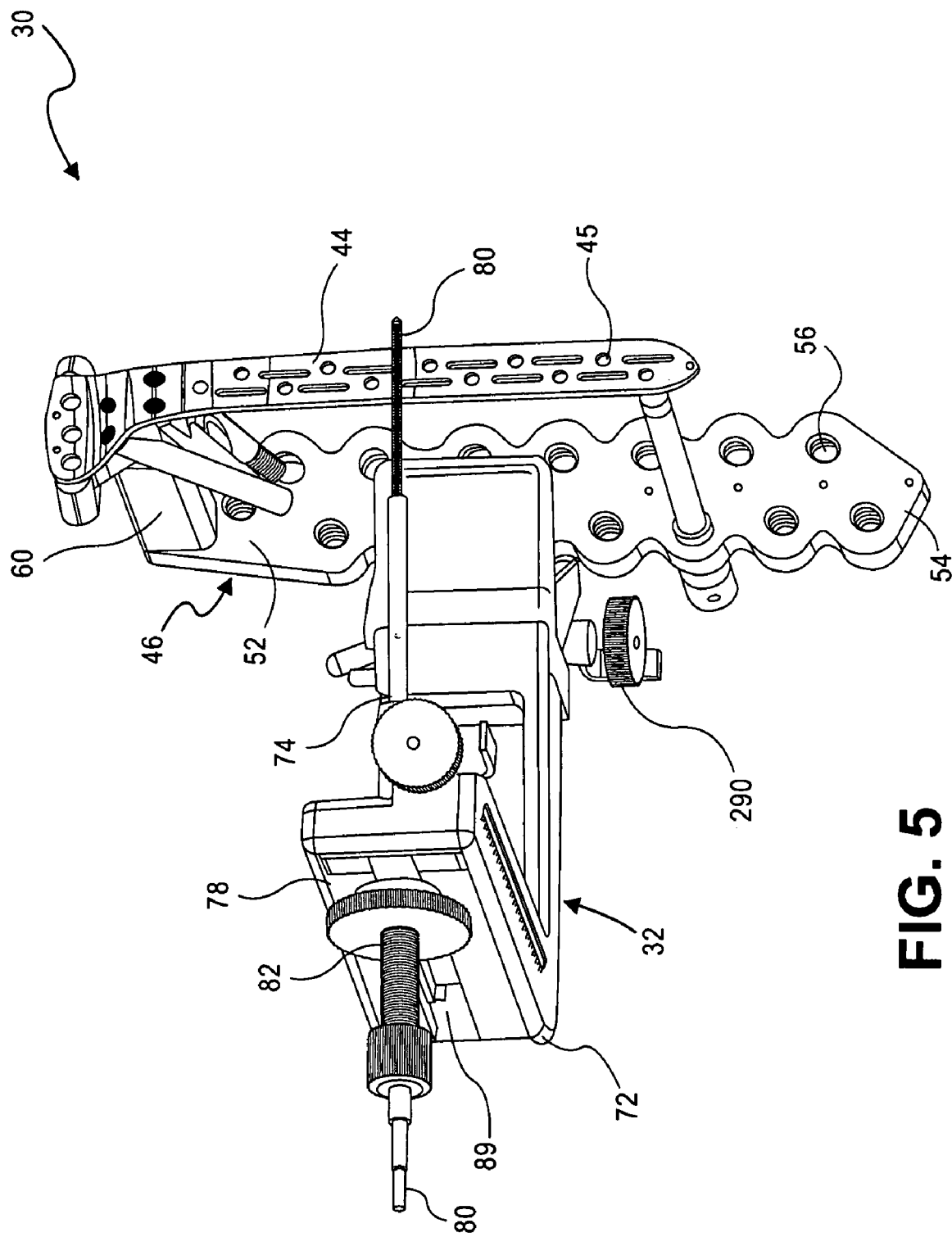
FIG. 5 is a side perspective view of the medical apparatus assembly of FIG. 1 taken along the line 5-5 of FIG. 2.

In general, the present invention relates to a medical apparatus assembly 30 and medical apparatus 32 for use with a segmented bone, for example a fractured or osteotomised bone, and preferably for use in repositioning a second bone portion 34 in relation to a first bone portion 36. It is understood, that additional bone portions may be included and manipulated by the medical apparatus assembly 30 described herein, including third bone portions, fourth bone portions, and additional bone portions. In the figures and description, the embodiment described and illustrated herein is for use with a long bone, such as a tibia, having a longitudinal axis 38, and a fracture to create a first bone portion 36 and second bone portion 34. The bone further has a periphery 40 relative to the longitudinal axis 38. In particular, the apparatus 32 and assembly 30 are illustrated in use with both a right tibia bone plate, in FIGS. 1-5, and a left tibia bone plate, in FIGS. 16-23. However, it is appreciated that the medical apparatus 32 of the invention can be used on any bone in a mammalian body, including, but not limited to, a humerus, radius, ulna, femur, fibula, or tibia. The illustrated left tibia in FIGS. 16-23 is broken approximately seven to ten centimeters below the top 42 of the tibia. However, it is understood, that different locations of facture, osteotomy, types of fracture or separation, and different numbers of bone portions or fragments or segments would not depart from the overall scope of the medical apparatus and assembly disclosed.

An outrigger such as a bone plate 44 and a targeting jig 46 are included in a first mechanical assembly 48 of the medical apparatus assembly 30, and can be seen in FIGS. 1-5. The bone plate 44 may be any commercially available bone plate for securing and aligning the first bone portion or piece 36 and the second bone portion or piece 34. The bone plate 44 or other outrigger is affixed to the bone with at least one and preferably a plurality of fastening screws 50. The bone plate 44 and screws 50 are preferably comprised of a rigid material, such as titanium or stainless steel. However, it is contemplated that plastics, composites, resorbable materials, metals and/or other materials or combinations thereof which are suitable for insertion within a mammalian body may be used for one or more of the components of the bone plate 44. For example, the bone plate and bone screws can be of the type substantially as described in U.S. patent application Ser. No. 11/588,037 filed Oct. 25, 2006, which is herein incorporated in its entirety by reference.

Attached to the bone plate 44 is the plate screw targeting jig 46, which can be a generic jig currently available from many suppliers. The targeting jig 46 illustrated herein, as best seen in FIG. 1, includes a lower portion 52 longitudinally separated from an upper portion 54, and has a length sufficient to facilitate the attachment of longitudinally disposed the bone plate 44 to the assembled bone portions 34, 36. The jig 46 illustrated includes an array of apertures 56 spaced along its length. The apertures 56 may be spaced both longitudinally and laterally. The apertures may comprise a bore, for example to receive a bushing such as of the type disclosed in U.S. patent application Ser. No. 11/588,037 filed Oct. 25, 2006 or threaded bore. The bores or threaded bores 56 may receive a drilling sleeve or fixation bolt 58 or other attachment device for use in attachment of the bone plate 44 to the bone portions 34, 36. Attached to the lower portion 52 of the targeting jig 46, and preferably near the end thereof, is an arm 60 for attachment of the bone plate 44 to the targeting jig 46. The arm 60 has a first end 62 which receives a fastener 64, such as a threaded fastener that can be rotationally inserted through a threaded bore 56 of the targeting jig 46 and into the first end 62 of the arm 60 to attach the arm to the jig 46. The second end of the arm 60 includes a bone plate receptor 66 to receive a portion of the bone plate 44. Preferably, the bone plate receptor 66 includes a portion contoured to correspond to the contour of the bone plate 44 used. In this regard, the arm 60 may be varied to accommodate alterative bone plates 44 selected and the contour thereof. One or more sleeves 68, such as drilling sleeves, may be operably attached to the bone plate receptor 66 to facilitate or guide the drilling of target openings in the bone portion 34 for attachment of bone screws 50 to the bone piece. Likewise, one or more fasteners, such as a short connection screw 70, may be attached to the arm 60 or bone plate receptor 66.

The medical apparatus 32 of the invention includes a central portion or framework or bridge 72 having a first end portion 74 coupleable to the targeting jig 46 by a first fastening assembly 76 and a second end portion 78 coupleable to a half pin or pin 80 by means of a second fastening assembly 82. The first fastening assembly 76 is part of the first mechanical assembly 48, while in the illustrated preferred embodiment medical apparatus 32 is composed of bridge 72, first and second fastening assemblies 76 and 82 and pin 80. In one embodiment, the bridge 72 further includes an intermediate portion 84 positioned between the first end portion 74 and the second end portion 78. The intermediate portion 84 positions the second end portion 78 of the bridge 72 at an angle 86 extending away from the first end portion 74 of the bridge 72. In a preferred embodiment, this angle is approximately ninety degrees, so that the first end portion 74 of the bridge 72 extends perpendicular to the second end portion 78 of the bridge 72. As such, the bridge 72 is preferably L-shaped in conformation with a first segment 87 having a length ranging from ten to forty centimeters and preferably approximately twenty centimeters and a second segment 93 having a length ranging from ten to forty centimeters and preferably approximately twenty centimeters. In addition, the bridge 72 preferably has an L-shaped cross section.

The medical apparatus 32 is preferably made from components of one or more rigid materials to provide for precise movement of the second bone portion 34 relative to the first bone portion 36. For instance, the bridge 72 may be composed of a titanium, steel, or plastic, so as to limit the flexibility of the bridge 72. Although the bridge 72 is shown and described as having an L-shaped configuration, it is appreciated that the bridge can have an arcuate configuration or be of any other suitable configuration for positioning first and second fastening assemblies 76 and 82 relative to each other and thus the portions or the bone being reduced or otherwise repositioned relative to each other.

Figure 6:
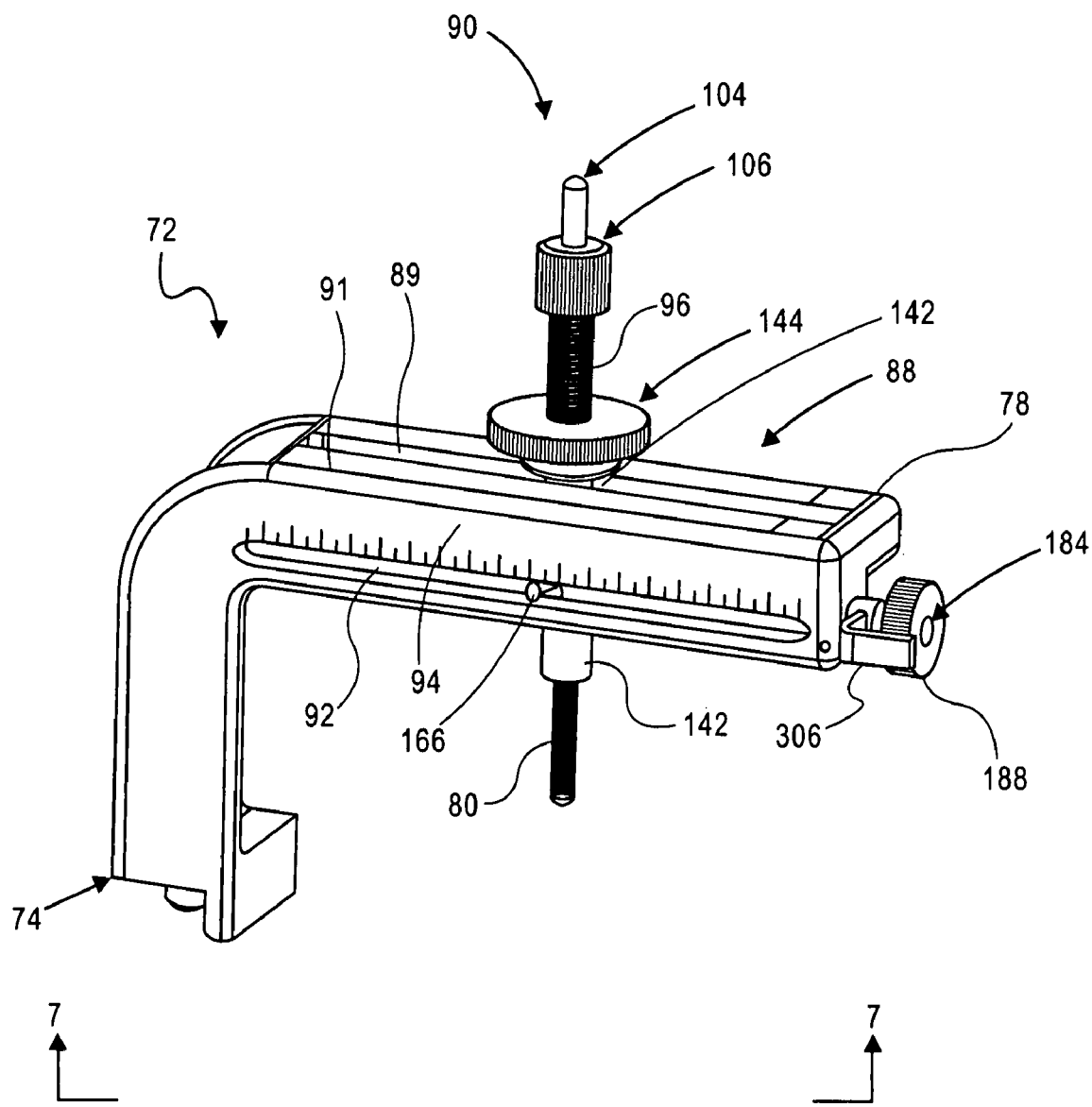
FIG. 6 is an enlarged bottom plan view of the bridge of the medical apparatus assembly, together with the pin and the related fastening and adjustment assemblies, of FIG. 1.

The first end portion 74, second end portion 78 and intermediate portion 84 of the bridge forms a length sufficient to extend around a portion of the periphery 40 of the bone. The bridge 72 extends around a portion of the periphery 40 of the bone when placed in its operational position, which is spaced radially from the bone. The second end portion 78, as can be seen in FIGS. 6-7, carries a second mechanical assembly 88 of the medical apparatus assembly 30 which is coupleable to the second portion 36 of the bone. The second mechanical assembly 88 includes the second fastening assembly 82 carrying pin 80. The second end portion 78 of the bridge 72 includes a slot 89 through a surface 91 of the second end portion 78 of the bridge 72 extending longitudinally along a distance of its length for carrying an adjustment assembly 90. The slot receives the at least one adjustment assembly 90, which carries the second fastening assembly 82, and is positioned in surface 91 and sized for lateral movement of the second fastening assembly 82 within the second end portion 78. A second slot 92 is provided in a second surface 94 of the second end portion 78 of the bridge 72, which slot receives a portion of the adjustment assembly 90. Additional slots and/or openings or apertures may be provided in the second end portion 78 on the same or alternate surfaces for viewing and/or measurement of the positioning of the adjustment assembly 90, or for access to the components thereof.

Figure 10:
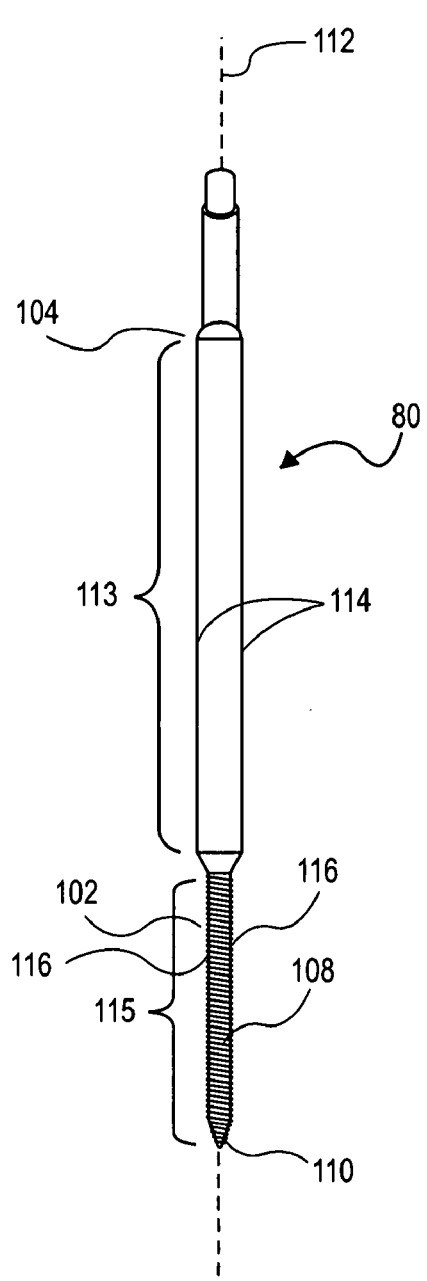
FIG. 10 is a side elevational view of the pin of FIG. 6.

The second fastening assembly 82 carried by the adjustment assembly 90 includes a spindle 96, as seen in FIG. 8, having a first or distal end 98 and a second or proximal end 100, and through which the pin or elongate pin 80, as seen in FIG. 10 and having a first end portion or distal end 102 and a second end portion or proximal end 104, extends. A spindle nut 106 (FIGS. 6, 8 and 9) is operably attached at one end of the spindle 96 so as to clamp or couple the proximal end portion of the spindle 96, to the framework 72. The distal end portion 102 of the pin 80 has an outer thread 108 and a sharpened tip 110 for penetrating, or engagement with and attachment to the second bone portion 34 (see FIG. 10). The proximal end portion 104 of the pin 80 extends beyond the spindle nut 106 for engagement with a drill (not shown) and/or may be manually gripped by the user. The pin 80 has a longitudinal axis 112 extending from the proximal end portion 104 to the distal end portion 102 of the pin 80, and is preferably made from any suitable rigid material such as metal, more preferably titanium or stainless steel. The pin has a portion 113, positioned along an intermediate portion of the pin, with a first width 114 which is greater in diameter than a second width 116 of a second portion 115, positioned at the distal portion 102 of the pin. The first width 114 is preferably four to six millimeters. The second width is preferably four to six millimeters. The pin 80 preferably extends a length ranging from one-hundred millimeters to two-hundred fifty millimeters and preferably approximately one-hundred and eighty millimeters.

The distal end 98 of the spindle 96 includes an inwardly tapered portion 118 having longitudinally extending slots 120 radially spaced thereon. Adjacent the tapered portion 118 is a first threaded portion 122 having external threads 124 forming a first outer diameter. A second threaded portion 126 is positioned adjacent the first threaded portion 122. The second threaded portion 126 has external threads 128 forming an outer diameter smaller than the outer diameter of the first threaded portion 122. The second threaded portion 126 may include one or more slots or grooves 130 extending longitudinally, substantially the length of threaded portion 126. The spindle 96 is preferably made from any suitable rigid material such as metal and more preferably titanium or stainless steel, and is preferably of a length of approximately one-hundred fifty to two-hundred fifty millimeters. The spindle 96 more preferably has a length from fifty to two-hundred fifty millimeters, and width of seven to fifteen millimeters. The shape of the spindle has a grove that does not allow the spindle to rotate as the spindle is moved up and down with elevation knob 144. An outcropping within the trolley 142 is provided that grove 130 fits over, which does not allow the spindle to spin but translates it up and down.

The spindle nut 106 includes a first end portion 132 having an inner thread portion 134 sized to receive the second threaded portion 126 of the spindle 96. An aperture or tapered opening 136 is positioned adjacent the threaded portion 134 in the second end portion 138 of the nut. The outer circumference of the spindle nut 106 includes ridges 140 for hand operation of the nut 106 by the user. The spindle nut 106 is preferably composed of titanium or stainless steel, or may be composed of plastic or other metals.

The adjustment assembly 90 further includes an elevation adjustment mechanism comprising a trolley 142, carried by the second end portion 78 of the framework 72, and an elevation adjustment knob 144. The trolley 142, as best seen in FIG. 8, includes a pin or spindle engaging portion 146 having a throughbore 148 or channel with a first end 150 and a second end 152, and preferably having a cylindrical cross-section, for receipt of the spindle 96, which extends through the trolley 142. The throughbore 148 may have an internal thread, or may have a substantially smooth surface. A bridge engagement mechanism 154 is carried by the trolley 142 at a position between the first end 150 and the second end 152 of the trolley 142. The bridge engagement mechanism 154 includes a slide member 156 and a guide member 158. The slide member 156 has a first end portion, or first wing 160, and a second end portion or second wing 162, which wings extend outwardly from the pin engaging portion 146 of the trolley 142, and which are shaped to fit and slide within slot 89 in surface 91 of the bridge 72. Preferably, the slide member 156 comprises a substantially rectangular cross-section, and may include inner grooves 164, 166 within the first side portion 160 and second side portion 162 of the slide member 156 for compression of thereof. The guide member 158 comprises a perpendicularly disposed protrusion 168 extending from the pin engaging portion 146 of the trolley, a portion of which is positioned and shaped to fit within the second slot 92 in second surface 94 of the bridge 72. The guide member 158 may be used to provide a secondary contact point of the trolley 142 with the bridge 72 at a position substantially perpendicular to the engagement with the first slot 89 and may also be used to determine the lateral position of the adjustment assembly 90. The trolley 142 further includes a throughbore 170 for receipt of a screw, such as a long metering screw 172, which when rotated causes the trolley 142 to move laterally along the screw. The throughbore 170 is positioned in an arm 174 of the trolley 142, and includes an inner thread 176 for engaging an outer thread 178 of screw 172.

The elevation adjustment knob 144 shown in FIG. 8 has an inner spindle/trolley engagement portion 180 and an outer ridge 182 for hand operation by the user. The elevation adjustment knob 144 is threaded about external threaded portion 126 of the spindle 96 extending through the trolley 142, and is rotatably joined to the trolley 142 at the second end 152 for moving the pin 80 proximally and distally, or inwardly and outwardly, along its axis 112, relative to the trolley 142 and the framework 72.

Figure 11:
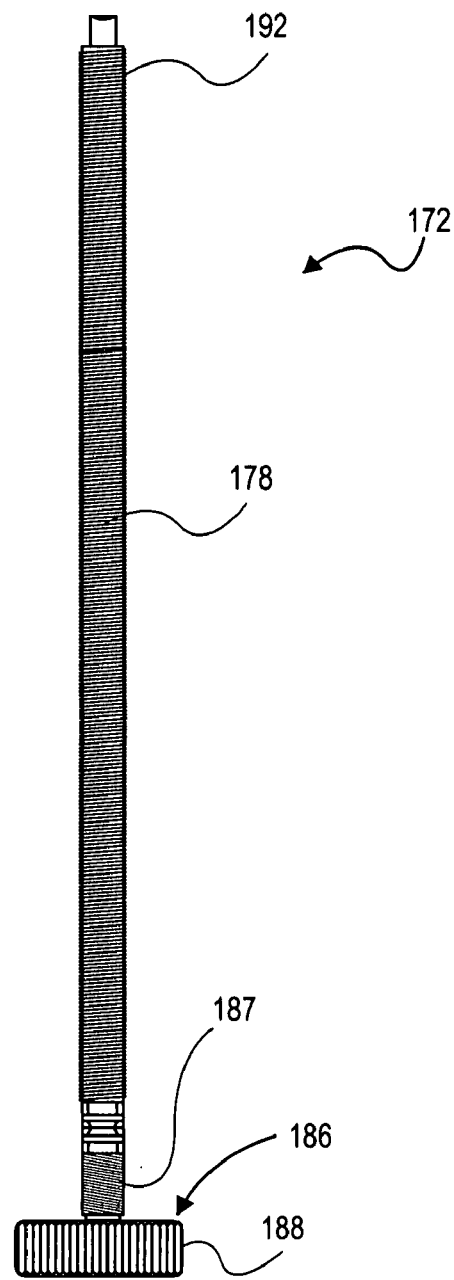
FIG. 11 is a side elevational view of the long metering screw of one of the adjustment assemblies of FIG. 6.

A second adjustment assembly or mechanism 184 or assembly capable of moving the pin 80 laterally relative to its axis 112, and perpendicular to the movement of the first adjustment assembly 90, includes a the long metering screw or medial/lateral spindle 172 (FIG. 11) which carries a medial/lateral adjustment knob 186 at a first end 187 of the screw extending beyond the second end portion 78 of the framework. Trolley 142 is also included in the second adjustment assembly 184. The medial/lateral adjustment knob 186 includes an outer ridge 188 for hand operation by the user. The long metering screw 172 is carried by and extends through opening 190 in the second end portion 78 of the framework 72. The long metering screw outer thread 178 corresponds to inner thread 176 of trolley arm throughbore 170. The screw 172 threadedly extends through the trolley arm throughbore 170, perpendicular to the spindle attachment, and extends along a length of the second end portion 78 of the framework 72 corresponding to at least a length of slot 89 provided in surface 91 of the bridge 72. The second end 192 of the screw is received in a receptor 194 located at or near intermediate portion 84 of the bridge 72.

At the first end portion 74 of the bridge 72, the first fastening assembly 76 is attached (see FIGS. 1 and 3-5). A male connector 196 is provided in surface 198 of the bridge 72, at the first end portion 74 of the bridge 72 for receipt by a corresponding female connector 202 in surface 204 of the first fastening assembly 76 (see FIGS. 7 & 12-13). More specifically, the female connector 202 resides in the base upper part 206 of the assembly 76.

Figure 12:
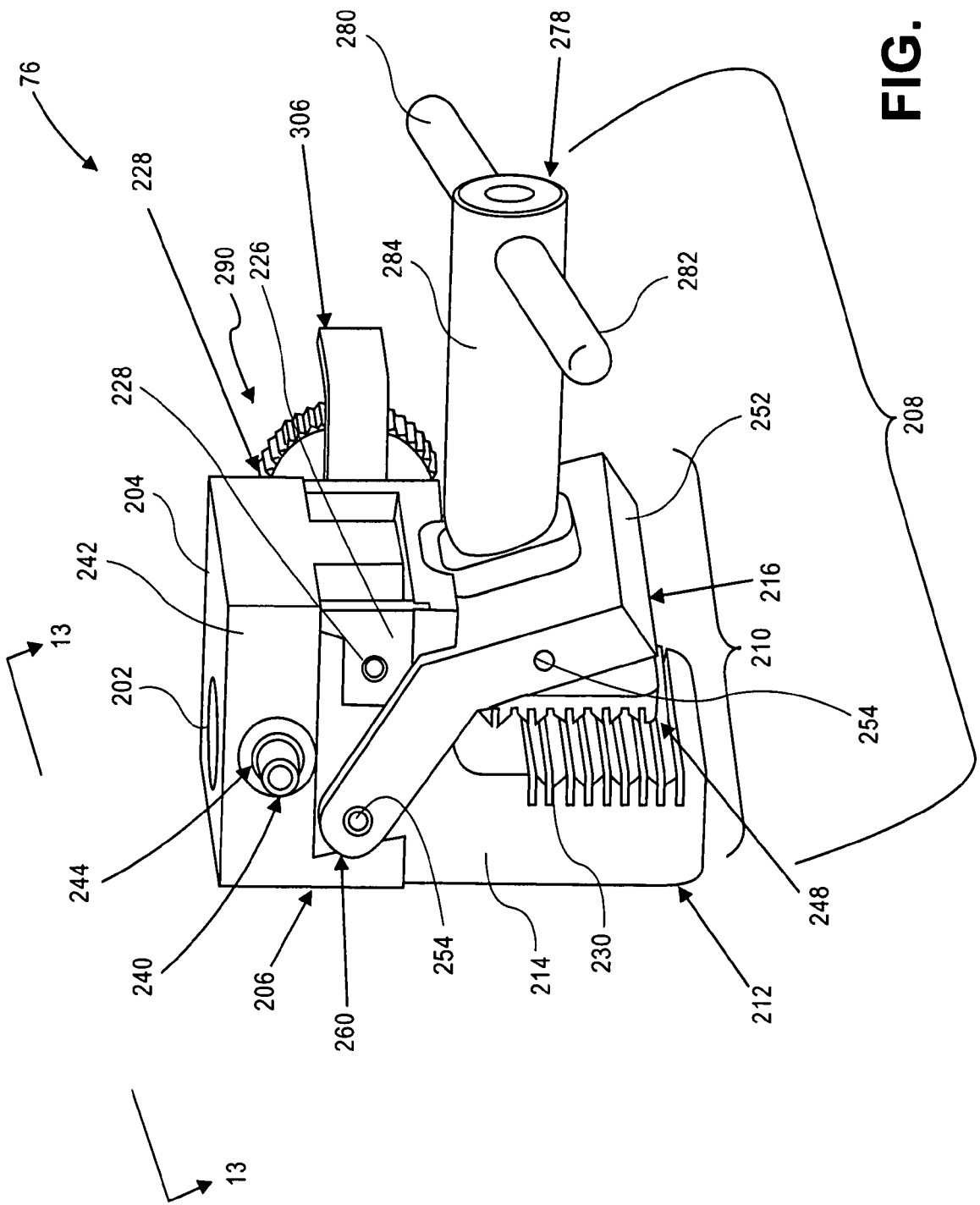
FIG. 12 is a top perspective view of another fastening assembly and adjustment assembly of the medical apparatus assembly of FIG. 1.
Figure 13:
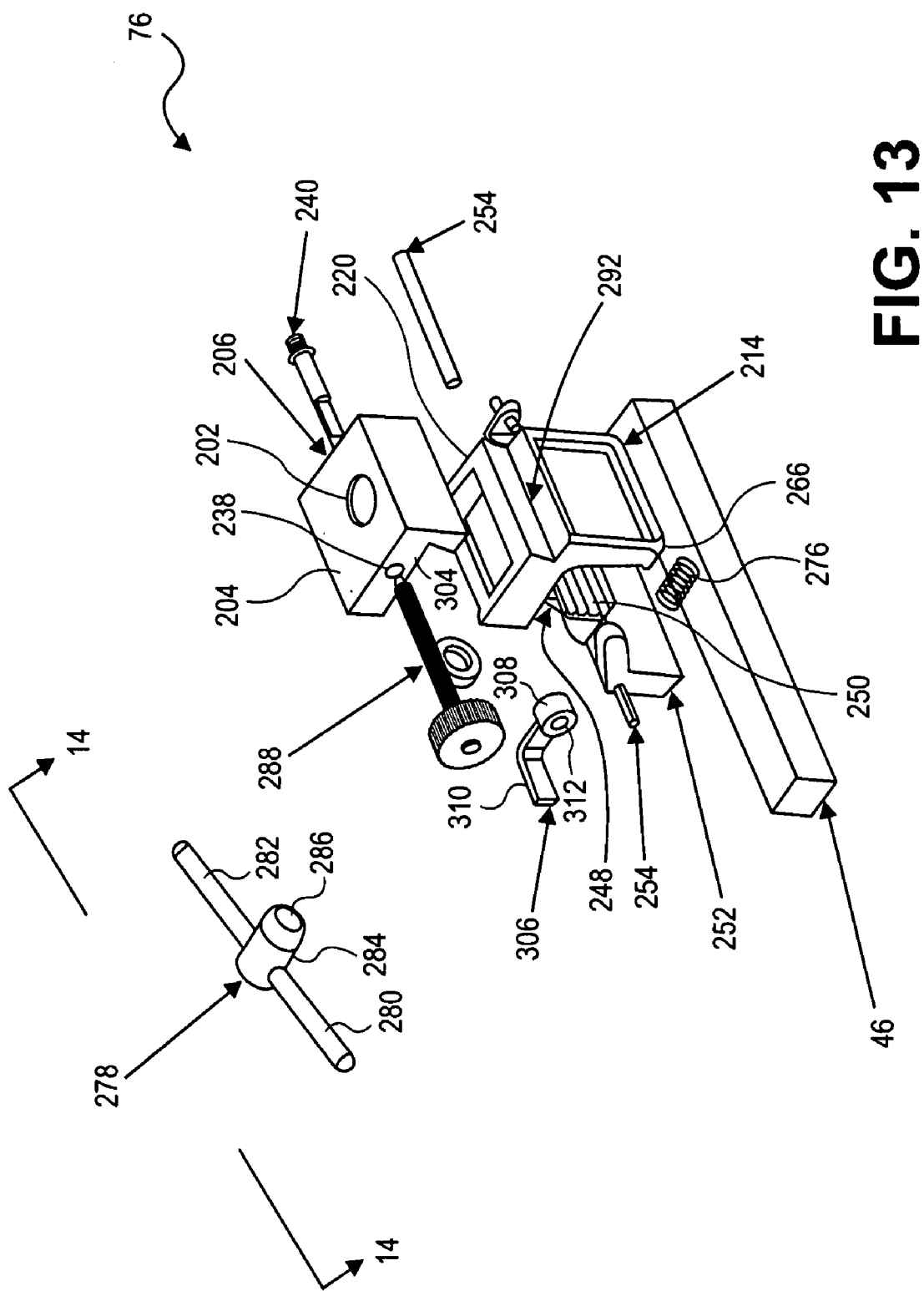
FIG. 13 is an exploded view of the fastening assembly and adjustment assembly of FIG. 12, taken along the line 13-13 of FIG. 12.

The first fastening assembly 76, as shown in FIGS. 12-14, includes the bridge clamp or clamping assembly 208 for attachment to the plate screw targeting jig 46. The first fastening assembly 76 is attached to the targeting jig 46 by a tightenable jaw assembly 210 included in the clamp assembly 208. The jaw assembly 210 has a stationary portion 212, formed on a base lower part 214, and a moveable jaw assembly 216. In this regard, first fastening assembly 76 including the jaw assembly 210 includes a base upper part 206 and a base lower part 214. The base upper part 206 is securable to the bridge 72 of the medical apparatus 32. The base lower part 214 is constructed for removable attachment to a targeting jig 46. The base lower part 214 may be easily disconnected from the base upper part 206 so that the base lower part 214 can be easily switched out with a different lower part configured for use with a different targeting jig 46 than the first base lower part 214. More specifically, the base lower part 214 forming a portion of the jaw assembly 210 is removably coupled to the base upper part 206 by means of a removable pin 240.

In detail, the base lower part 214 is provided with an attachment aperture or throughbore 218 in its upper portion 220 for attachment to the base upper part 206. The base upper part 206 includes a core 222 shaped to receive the upper portion 220 of the base lower part 214, a spindle receptor portion 224, and a threaded nut 226 for proximal/distal spindle 228. The base lower part 214 includes a jaw surface 230 on the stationary portion 212, which, in the illustrated embodiment, comprises a series of ridges or serrations. The base lower part 214 further includes an aperture 232 for receipt of the proximal/distal spindle or short metering screw 228. The aperture 232 may be threaded to receive an outer thread 234 of the spindle or screw.

The base upper part 206 includes a first alignment aperture or throughbore 238 for alignment with the attachment throughbore 218 of the base lower part 214 and for receipt of a pin 240, on a first side 242 of the base upper part 206, carrying a washer 244, such as a locking washer. The pin 240 removably connects the base lower part 214 to the base upper part 206 by being slidably received within the throughbores 218, 238 of the base upper part 206 and base lower part 214. The spindle receptor portion 224 is formed by second aperture or throughbore 246, aligned with throughbore 232 of the base lower part 214, for receipt of the proximal/distal spindle 228. The second aperture 246 may be threaded to receive the outer thread 234 of the spindle or screw and for lateral movement along the spindle.

The moveable portion 216 of the jaw assembly 210 includes a medial part 248 having a serrated or toothed surface that is pivotally coupled by at least one and preferably two pins and a moveable backing. More specifically, the moveable jaw assembly 216 is pivotally attached to the base lower part 214, and includes a medial part 248 having a series of ridges or serrations on a surface 250 facing the ridged surface 212 of the base lower part 214, and a moveable backing 252. The pivotal attachment is formed by a hinge pin 254 received in first and second apertures 256, 258 on first and second arms 260, 262 of the moveable backing 252 and a hinge pin receptor 264, 266 on the upper portion 220 of the base lower part 214. The medial part 248 which is carried by the moveable backing 252, is operably and pivotally connected by a first jaw holding pin 268 and a second jaw holding pin 270 received in aligned pin receptors 272, 274 on facing surfaces of the medial part 248 and the moveable backing 252. The pivotal attachments permit the moveable jaw assembly 216 to pivot so as to permit engagement of the jaw assembly 210 with the targeting jig. A spring 276, such as a coiled spring, may be positioned and attached to the moveable jaw assembly 216 for recoil of the medial jaw 216 or 248 relative to the lateral jaw 212.

The moveable jaw 216 may be further engaged by a metering nut or nut or jaw clamp press 278 of the clamping assembly 208, which can be tightened by hand for urging the moveable jaw assembly 216 toward the stationary portion 212 of the jaw assembly 210. The jaw clamp press 278 is rotatably carried by threaded rod 279. The jaw clamp press 278 includes a hand engagement means, such as a pair of outwardly extending arms 280, 282 positioned on a shaft 284, and an engagement end 286, engagable with the moveable backing 252 of the moveable jaw assembly 216. A washer 288, such as a locking washer, may also be provided between the moveable backing 252 and the shaft 284.

A third adjustment assembly 290 of the medical apparatus 32, capable of moving the pin 80 laterally relative to its axis 112 and in a direction perpendicular to the proximal/distal adjustment of the pin 80 by adjustment assembly 90 and perpendicular to the medial/lateral adjustment of the pin 80 by second adjustment assembly 184, is carried by the clamping assembly 208 at the first end 74 of the bridge 72 or framework. The third adjustment assembly 290 includes proximal/distal or upward/downward adjustment mechanism carried by fastening assembly 76. The adjustment mechanism includes a rail 292 allowing proximal and distal migration of the bridge 72 relative to the targeting jig 46. The assembly includes proximal/distal spindle or knob 228, as shown in FIG. 15, the rotation of which causes the framework 72 to move proximally or distally relative to the targeting jig 46. More specifically, the spindle 228 has a first end 294 and a second end 296, and includes a knob 298 secured to the second end 296 of a threaded shaft 302. The knob may include an outer ridge 303 for hand manipulation by the user. The threaded shaft 302 is rotatably received at a second side 304 of the base upper part 206 by the throughbore 232, 246 and is received in the threaded nut 226. Specifically, the threaded shaft threadedly engages the threaded nut in the base upper part 206 of the jaw assembly. The base upper part 206 slidably engages the base lower part 214, and is moveable proximally and distally relative to the base lower part 214 and therefore the targeting guide, by rotation of the proximal/distal spindle 228.

A proximal/distal spindle locking nut 306 is carried by the base lower part 214 and includes a securing portion 308 for securing the spindle 228 in position in the base lower part 214 and an arm 310 for engaging and locking the nut 306 with the spindle 228. The securing portion 308 preferably comprises an aperture 312, such as a centralized aperture and may include an inner thread. The threaded aperture 312 receives the outer thread 234 of the short metering screw or proximal/distal spindle 228, and rotates about the longitudinal axis 314 of the spindle, so as to frictionally engage the base lower part 214 and prevent further movement of the spindle 228.

The first fastening assembly 76 is attached to targeting jig 46 by inserting a portion of targeting jig 46 into the space provided between the stationary portion 212 of the jaw assembly 210 and the moveable jaw assembly 216 of the jaw assembly 210 so that the jaw surface 230 and jaw surface 250 are positioned to engage first and second opposing surfaces 251 and 253 of the targeting jig. The metering nut or jaw clamp press 278 is grasped by hand and moved to urge the moveable jaw assembly 216 toward the stationary portion 212 of the jaw assembly 210. Rotation of jaw clamp press 278 over threaded rod 279 causes the jaw 216 to open and close. For instance, the movement of jaw clamp press 278 causes movement of the moveable jaw assembly 216 to pivot toward the stationary jaw thereby tightening the clamp holding the targeting jig in place.

In the illustrated method of use of the medical apparatus assembly 30 and medical apparatus 32 thereof, the illustrated left tibia in FIGS. 16-22 is broken approximately seven to ten centimeters below the top 42 of the tibia and the piece 34 that is broken is translated medially, distally and posteriorly because the distal bone piece 34 is medial, distal and posterior to the proximal bone piece 36.

In one preferred method of the use of the medical apparatus assembly 30 and medical apparatus 32 thereof, illustrated in part in FIGS. 16-24 with respect to a segmented left tibia, an incision is made in the tissue in a location near the proximal portion 36 of the bone. For example, the incision may be three or four centimeters long. The bone plate 44 is inserted percutaneously into the body and fixed to the proximal piece 36 of bone in a position that allows the operating physician to control the proximal piece of bone. The bone plate 44 is also configured so that once the distal or broken piece 34 of the bone is repositioned next to the plate 44, the bone will be straight. The bone plate 44 is attached to the arm 60 of the targeting jig 46 via short connection screws 70, and is aligned with the targeting jig 46 so as to align the apertures 45, 56 in each respective device. A bone plate 44 is shown attached to the proximal or top piece 36 of the bone with screws 50 that are inserted through apertures 45 in the plate. The framework or bridge 72 of the medical apparatus 32 is disposed outside of the body and is attached to the targeting jig 46 via the clamp or clamping assembly 208 by using the metering nut 278 to tighten the jaw assembly 210 included in the clamp.

A small additional incision is made with a scalpel near the distal piece 34 of bone to allow the sharpened distal end portion 104 of the half pin 80 to be drilled through the spindle 96, which is seated in the trolley 142, into bone portion 36. Once the pin 80 is drilled into the bone, the spindle nut 106 is tightened to capture the distal end portion 104 of the half pin 80. The second portion 34 of the bone may be rotated about the pin 80.

Manipulation of the medical apparatus 32, for example by means of at least one adjustment mechanism, causes the pin 80 to move relative to the framework which causes the second or distal portion 34 of the bone to move and be repositioned relative to the first or proximal portion 36 of the bone. This is due to the attachment of the bridge 72 or framework to the targeting jig 46, which is attached to the bone plate 44 fastened to the first portion 36 of the bone.

At least one, and preferably three adjustment mechanisms are used to move the distal end portion 104 of the pin 80, which is operably attached to the bridge 72 of the medical apparatus 32, in three orthogonal directions, relative to the first mechanical assembly 48 or first end portion 74, so as to move the distal bone portion 34 to a position adjacent the proximal bone portion 36 and the bone plate 44. FIGS. 16-20 show the distal portion of the bone being moved in two directions, from a first position (shown in FIGS. 16-17) to a fourth, reduced position (shown in FIGS. 21-22). The distal bone portion 34 is translated, through a series of movements, to a position in engagement with the proximal portion 36 of the bone. As illustrated in FIGS. 16-22, to elevate the bone, for example, to bring the bone portion 34 forward or backwards (or anterior or posterior), the elevation adjustment knob 144 and mechanism is used. Rotation of the elevation adjustment knob 144 causes the pin 80 to move in a direction perpendicular to the second end 78 of the framework. Medial or lateral movement of the second bone portion or distal portion 34 is accomplished by manipulation of the medial/lateral adjustment mechanism 184. Namely, rotation of the medial/lateral adjustment knob 186 attached to the long metering screw 172 results in medial or lateral movement of the trolley 142 carrying the spindle 96 and pin 80, which trolley 142 is slidably received within slot 89 and/or 91, and, therefore, results in medial or lateral movement of the second portion 34 of the bone which may be inside relative to the body or toward the mid-line or outside relative to the body or away from the mid-line in the body. As a result, rotation of the medial/lateral knob 186 at the end of the long metering screw 172 causes the trolley 142 to move along the metering screw outer thread 178, thereby moving along the framework 72, which also causes the pin 80 carried by the adjustment assembly 90 to move laterally relative to the axis 112 of the pin 80. The third adjustment mechanism or proximal/distal adjustment mechanism 228 is manipulated by rotation of the proximal/distal adjustment knob 298 operably connected to the clamp assembly 208. This knob and spindle 228 moves the half pin 80 which is attached to the distal bone portion 34, relative to the bridge 72 and toward the bone plate 44, thereby reducing the distal portion of the bone, namely, placing the distal portion 34 of the bone in a proper anatomic position to heal.

Figure 16:
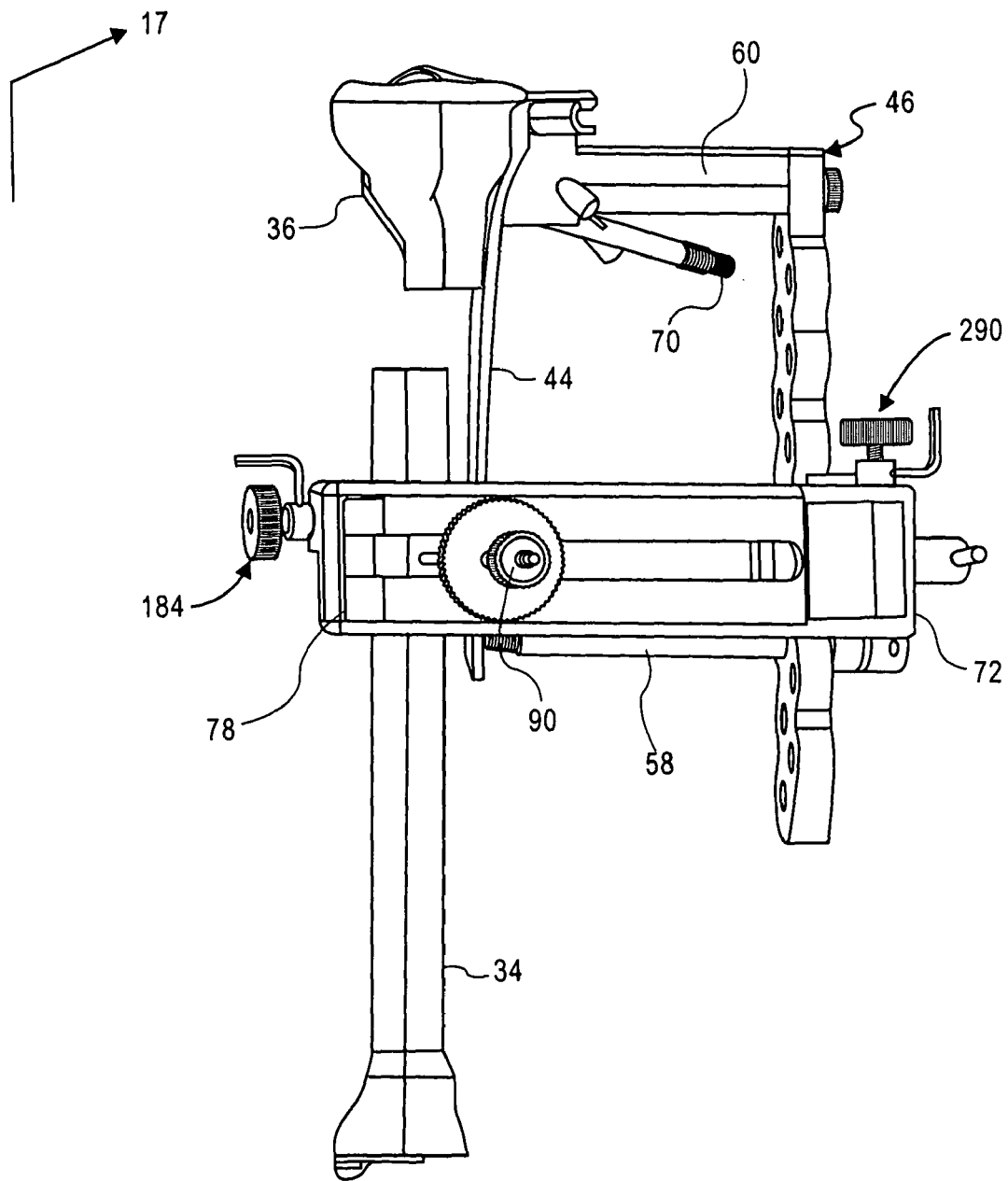
FIG. 16 is a front elevational view of the medical apparatus of the present invention coupled to a targeting jig secured to a left tibia bone plate and a proximal portion of a fractured left tibia, with the distal portion of the bone being disposed in a first position distally, laterally and anteriorly of the proximal portion of the bone.
Figure 17:
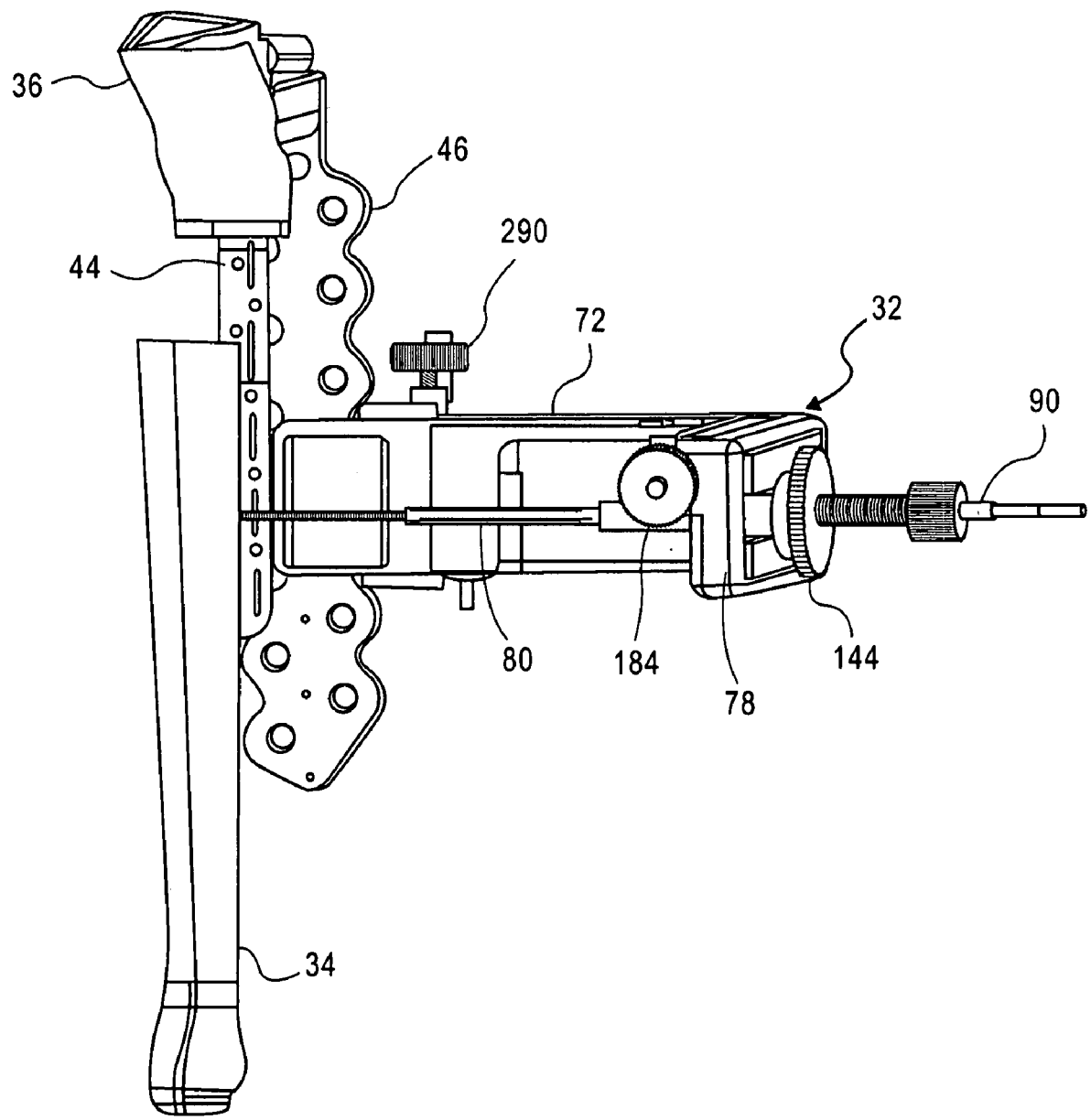
FIG. 17 is a side perspective view of the medical apparatus of FIG. 16 taken along the line 17-17 of FIG. 16 and showing the distal portion of the bone in the first position.
Figure 18:
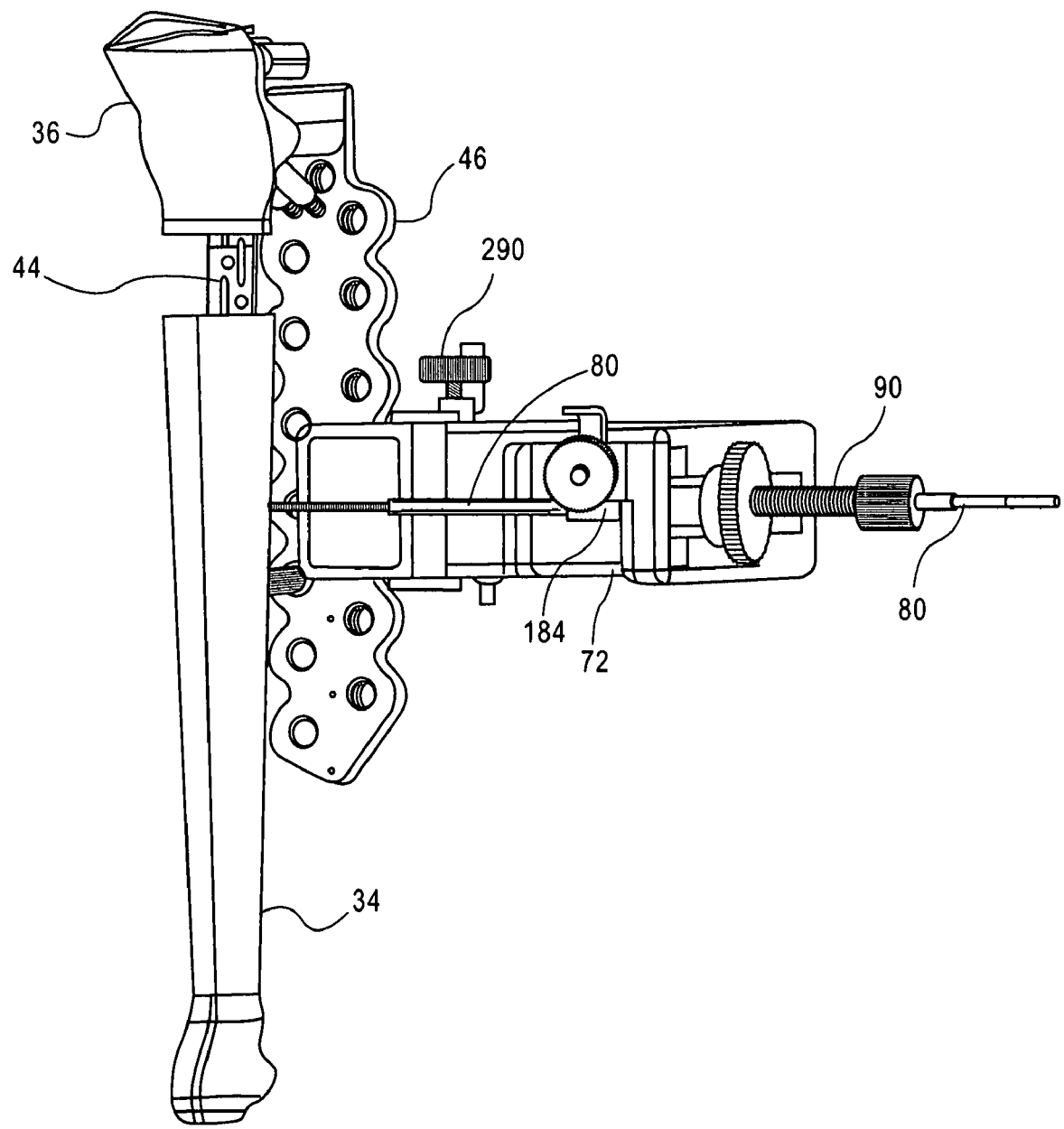
FIG. 18 is a side perspective view of the medical apparatus of FIG. 16 with the distal portion of the segmented bone moved anteriorly to a second position relative to the first position of FIG. 16.
Figure 19:
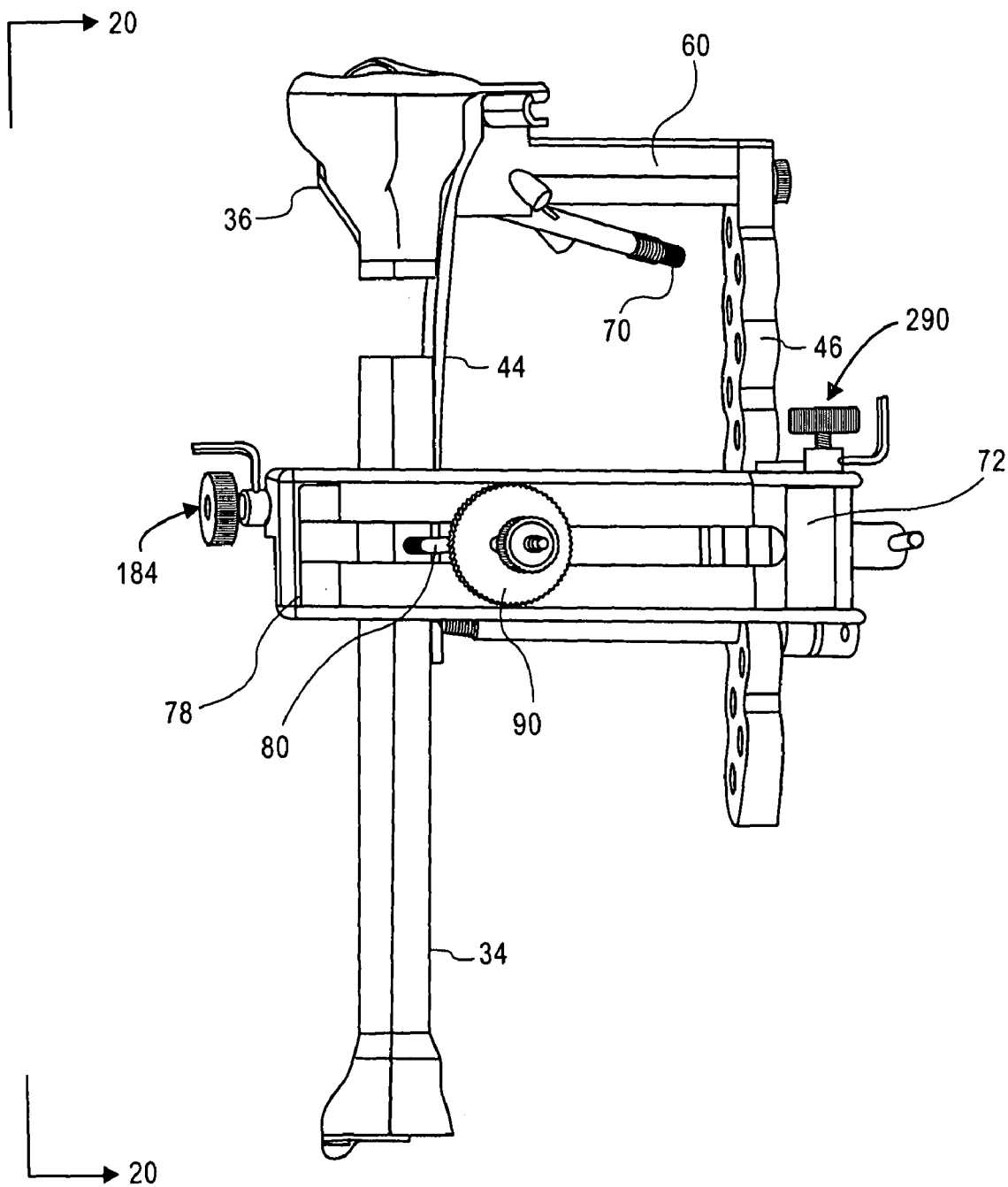
FIG. 19 is a front elevational view of the medical apparatus of FIG. 16 with the distal portion of the segmented bone moved laterally to a third position relative to the first position of FIG. 16.
Figure 20:
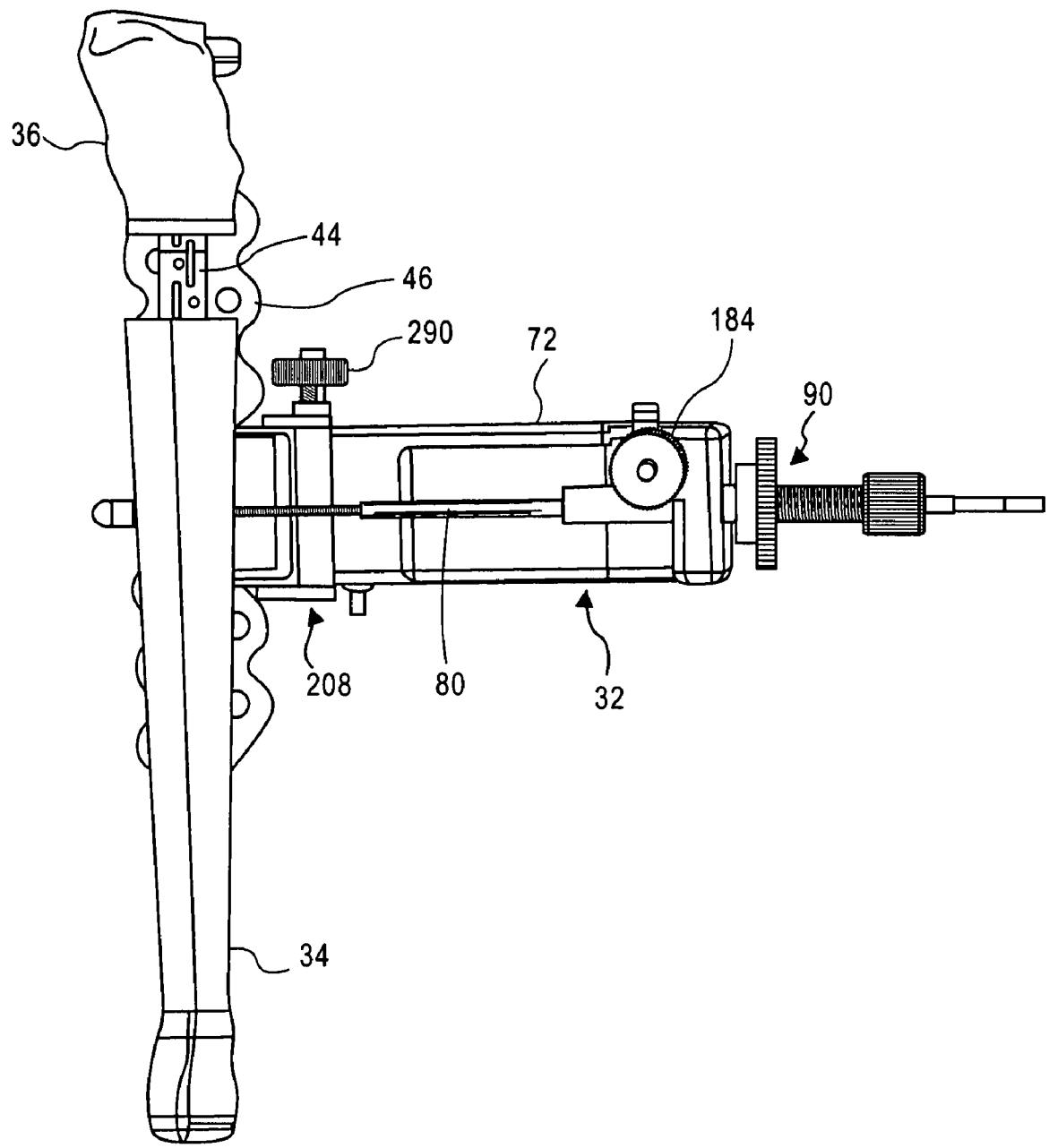
FIG. 20 is a side elevational view of the medical apparatus of FIG. 16 taken along the line 20-20 of FIG. 19 and showing the distal portion of the segmented bone in the third position.
Figure 21:
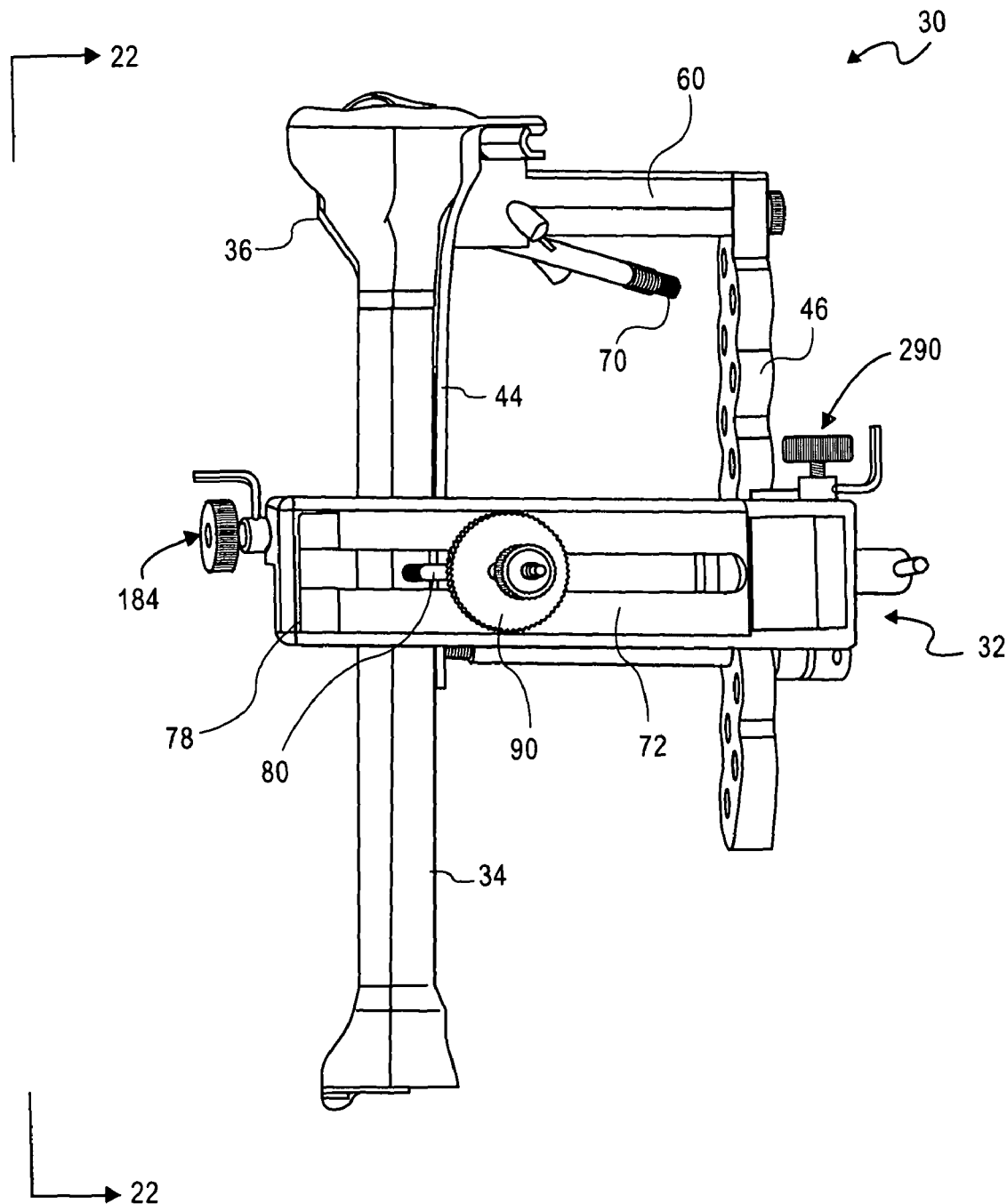
FIG. 21 is a front elevational view of the medical apparatus of FIG. 16 with the distal portion of the segmented bone moved proximally to a fourth or reduced position relative to the first position of FIG. 16.
Figure 22:
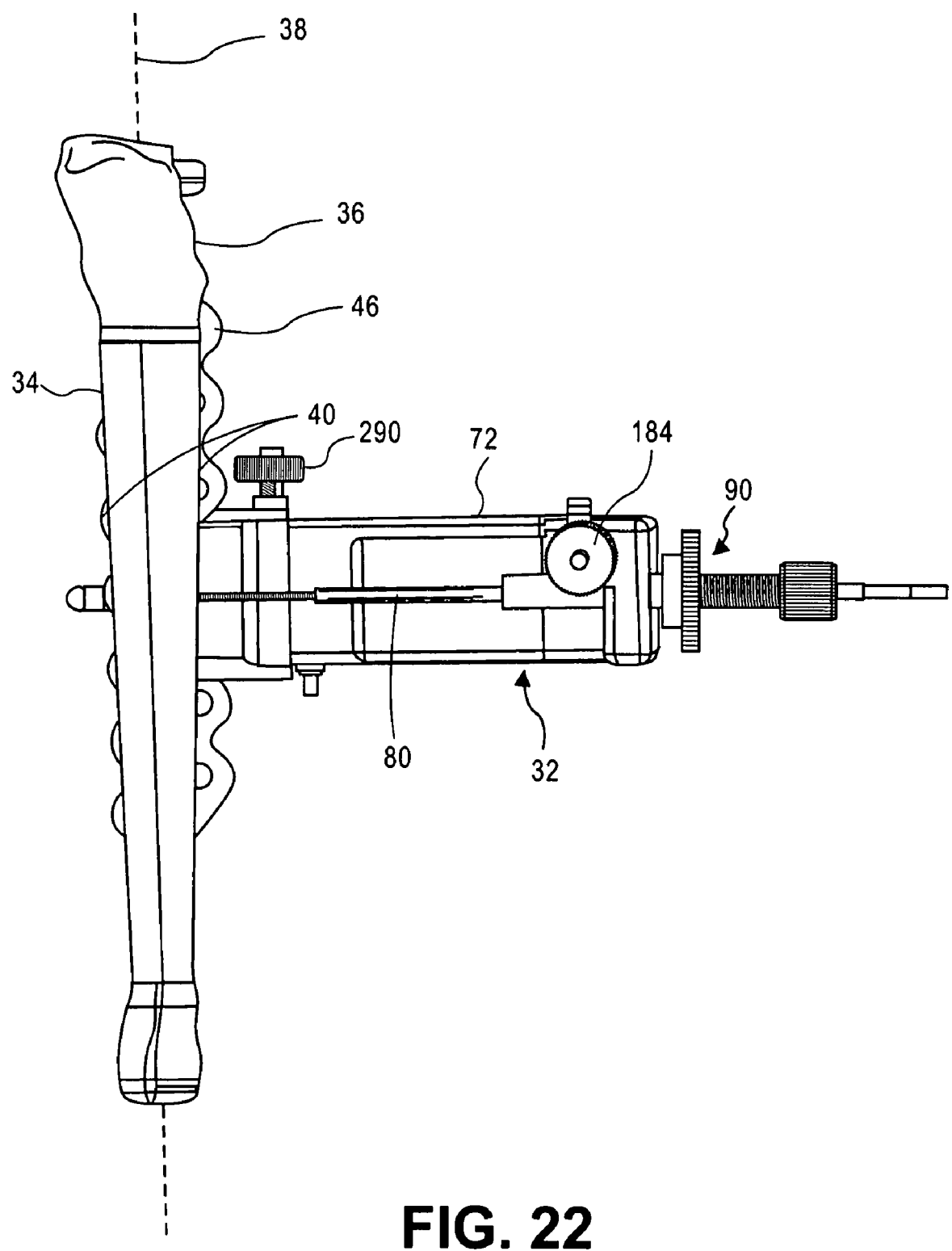
FIG. 22 is a side elevational view of the medical apparatus of FIG. 16 taken along the line 22-22 of FIG. 21 and showing the distal portion of the segmented bone in the fourth or reduced position of FIG. 21.

Thus, as can be seen by reference to FIGS. 16-18, the distal portion 34 of the bone which is disposed distally, laterally and anteriorly of the proximal portion 36 of the bone in the first position, is moved anteriorly to a second position relative to the first position. The distal portion 34 of the segmented bone is also moved laterally to a third position relative to the first position (see FIG. 19). The distal portion 36 of the bone may be moved proximally to a fourth or reduced position relative to the first position and into engagement with the proximal portion 36 of the bone (see FIGS. 21-22). Thus, as may be further seen with reference FIGS. 16-22, the distal portion 34 of the bone may be moved in multiple directions in order align the distal portion of the bone with the proximal portion 36 of the bone.

The distal portion 34 of the bone is subsequently affixed to the bone plate 44 by bone screws 50. In order to accomplish same, additional percutaneous incisions are made near the bone plate 44 and screws 50 (see FIG. 2) or fixation bolts 315 are inserted through appropriate apertures 45 in the bone plate 44 into the distal bone portion. The targeting jig 46 is used to assist in the accurate placement of the bone screws 50 into the bone plate 44 at the apertures.

It is appreciated that an additional medical apparatus, for example substantially similar to medical apparatus 32, can additional be coupled by means of its first fastening assembly 76 to the targeting jig 46 and thus the first bone portion 36 and be coupled by means of its pin 80 to the second bone portion 34 so as, together with medical apparatus 32, to rotate or otherwise perform complex manipulations of the second bone portion relative to the first bone portion.

Figure 23:
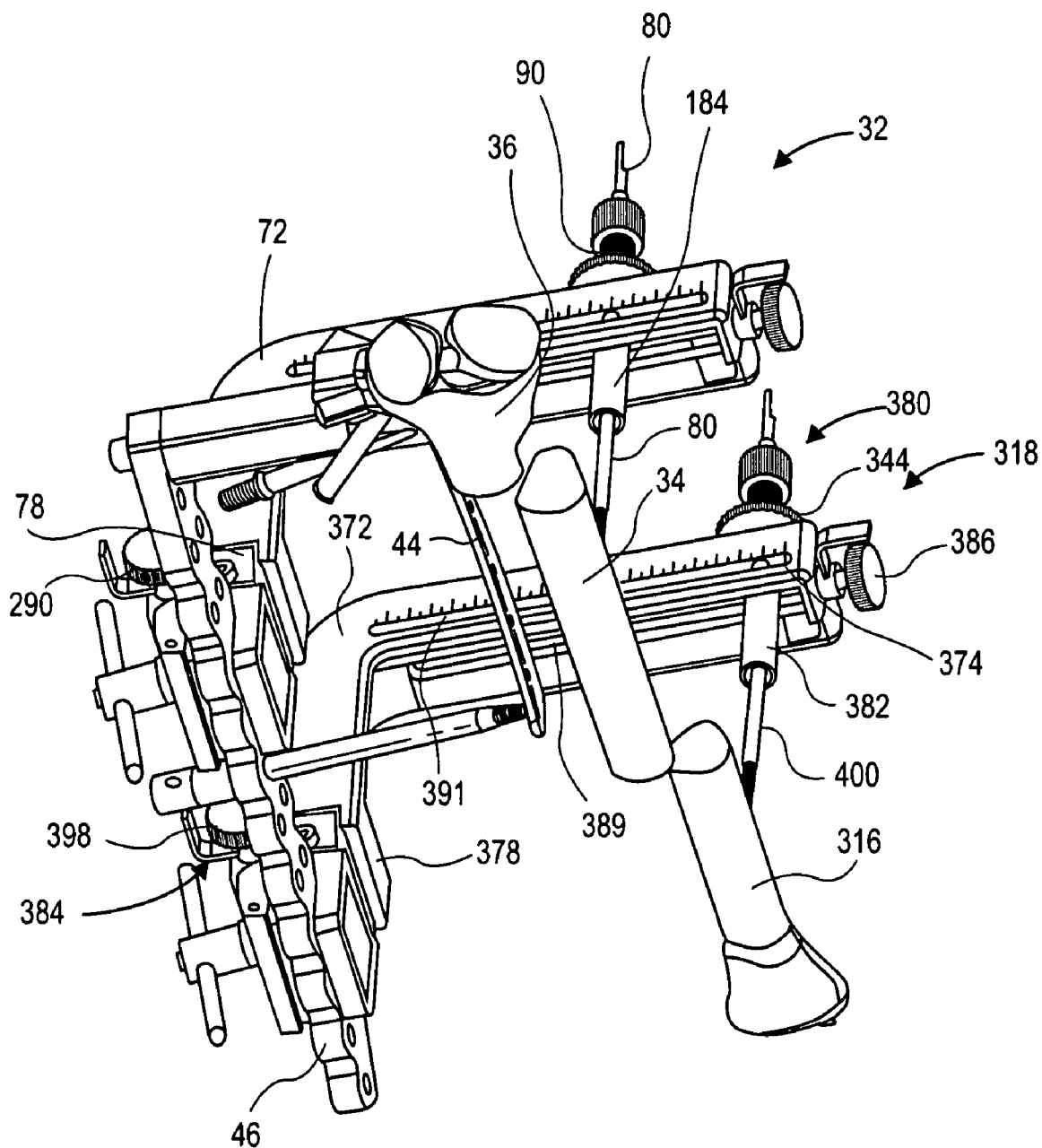
FIG. 23 is a side perspective view of the medical apparatus of the present invention coupled to a targeting jig secured to a left tibia bone plate and a proximal portion of a fractured left tibia, and having an additional medical apparatus, a first distal bone portion of the segmented bone being disposed distally and anteriorly of the proximal portion of the bone in a first position and a second distal bone portion of the segmented bone being disposed distally and anteriorly of the proximal portion of the bone in a first position.
Figure 24:
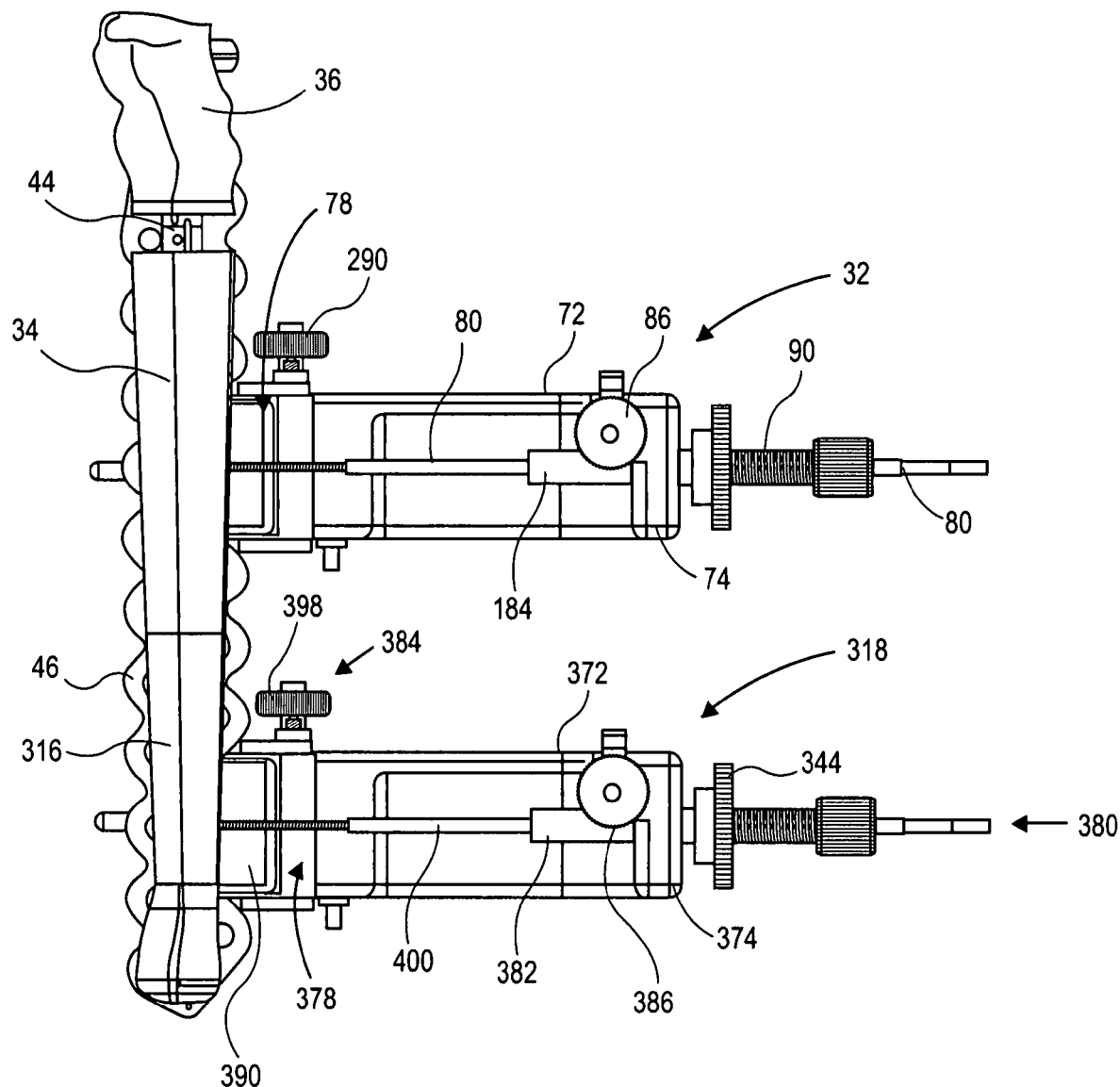
FIG. 24 is a side elevational view of the medical apparatus of FIG. 23 with the first distal portion of the segmented bone and second distal portion of the segmented bone each moved proximally to a second position relative to the first position of FIG. 23.

In the event that additional bone portions are present, such as, but not limited to, a third bone portion 316, as shown in FIGS. 23-24, an additional medical apparatus 318 substantially similar to medical apparatus 32 and having a central portion or bridge 372 may be coupled to the targeting jig 46, substantially as described above with respect to medical apparatus 32. The second end portion 378 of the medical apparatus 318 is attached to the third portion 316 of the bone substantially as described above with respect to medical apparatus 32. Manipulation of the medical apparatus 318 attached to a third bone portion 316 so as to reposition the third bone portion occurs substantially as described above with respect to medical apparatus 32. The additional medical apparatus 318 may have a first adjustment assembly or mechanism 380 substantially as described above with respect to medical apparatus 32, a second adjustment assembly or mechanism 382 substantially as described above with respect to medical apparatus 32, and a third adjustment assembly or mechanism 384 substantially as described with respect to medical apparatus 32 for moving the third bone segment 316 in three orthogonal directions, relative to the first mechanical assembly 380 of the additional medical apparatus 318 or first end portion 374, so as to move the third bone portion 316 to a position adjacent the proximal bone segment 36, distal bone segment 34, and the bone plate 44.

For example, to elevate the third bone portion 316 or to bring the bone portion 316 forward or backwards (or anterior or posterior), the elevation adjustment knob 344 and mechanism 380 is used. Rotation of the elevation adjustment knob 344 causes the pin 400 to move in a direction perpendicular to the second end 378 of the framework. Medial or lateral movement of the bone portion 316 is accomplished by manipulation of the medial/lateral adjustment mechanism 382. Namely, rotation of the medial/lateral adjustment knob 386 attached to a long metering screw results in medial or lateral movement of a trolley carrying the spindle and pin 400, which trolley is slidably received within slot 389 and/or 391, and, therefore, results in medial or lateral movement of the third portion 316 of the bone which may be inside relative to the body or toward the mid-line or outside relative to the body or away from the mid-line in the body. The third adjustment mechanism or proximal/distal adjustment mechanism 384 is manipulated by rotation of the proximal/distal adjustment knob 398 operably connected to the clamp assembly 390. This knob with attached spindle moves the half pin 400 which is attached to the bone portion 316, relative to the bridge 372 and toward the bone plate 44, thereby reducing the bone portion 316, namely, placing the bone portion 316 in a proper anatomic position to heal.

The additional medical apparatus 318 is independent of the first medical apparatus 32, and is, thus, operated independently. As a result, the bone segments 34, 316 may be moved separately. Specifically, bone segment 316 carried by the additional medical apparatus 318 may be moved in three orthogonal directions relative to bone segment 36 and relative to the bone segment 34. Similarly, the bone segment 34 may be moved in three orthogonal directions relative to bone segment 36 and bone segment 316.

An advantage of the medical apparatus 32 and medical assembly 30 as described and illustrated herein is that it allows percutaneous motion of the distal fracture using a device, which is less invasive and more accurate that traditional methods of repair. Furthermore, the device permits three orthogonal directions of movement of the fractured bone piece to accurately place the bone piece in the correct anatomic position to heal. In addition, the medical apparatus is versatile and usable with a variety of commercially available jigs and bone plates because the moveable jaw assembly 216, and portions thereof may be interchanged to accommodate a variety of assemblies of varying widths and configurations. The jaw assembly may also be configured for facilitating attachment of the medical apparatus 32 to a plurality of different types of targeting jigs. Moreover, the jaw assembly, and in particular the pivoting of the medial part 248 relative to the backing 252, facilitates a tight engagement between the jaw assembly 210 and the desired targeting guide or jig 46 to maintain accurate placement of the bone portions regardless of the jig and bone plate used.

Although medical apparatus assembly 30 has been shown and described as including, and medical apparatus 32 has been shown and described for use with, an outrigger such as a targeting jig 46 and a bone plate 44 and at least one fastening screw 50, it is appreciated that the outrigger of assembly 30 can include an external fixator (not shown) that is coupled to the bone by the at least one fastening screw 50 and preferably a plurality of fastening screws 50.

Although various representative embodiments of this invention have been described above with a certain degree of particularity, those skilled in the art could make numerous alterations to the disclosed embodiments without departing from the spirit or scope of the inventive subject matter set forth in the specification and claims. All directional references (e.g., upper, lower, upward, downward, left, right, leftward, rightward, top, bottom, above, below, vertical, horizontal, clockwise, counterclockwise, x-axis, y-axis, and z-axis) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected) are to be construed broadly and may include intermediate members between a connection of elements and relative movement between elements. As such, joinder references do not necessarily infer that two elements are directly connected and in fixed relation to each other.

In some instances, components are descried with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting.

Changes in detail or structure may be made without departing from the spirit of the invention as defined in the appended claims.

Although the present invention has been described with reference to preferred embodiments, persons skilled in the art will recognize that changes may be made in form and detail without departing from the spirit and scope of the invention.

What is claimed is:

1. A medical apparatus for repositioning first and second portions of a segmented bone of a mammalian body and for use with an outrigger coupled to the first portion of the bone with at least one fastening pin comprising a framework, a first fastening assembly adapted for coupling the framework to the outrigger whereby the framework can be coupled to the first portion of the bone by means of the first fastening assembly and the outrigger and at least one fastening pin, an elongate pin having first and second end portions, the first end portion of the elongate pin being provided with a sharpened tip for penetrating the second portion of the bone, a second fastening assembly for coupling the second end portion of the elongate pin to the framework whereby the framework can be coupled to the second portion of the bone by means of the elongate pin and the second fastening assembly and at least one adjustment assembly carried by at least one of the framework and the first and second fastening assemblies for moving the first end portion of the elongate pin relative to the outrigger so as to reposition the second portion of the bone relative to the first portion of the bone, wherein the elongate pin extends along an axis and the at least one adjustment assembly includes an adjustment mechanism for moving the elongate pin proximally and distally along the axis relative to the framework.

2. The apparatus of claim 1 wherein the adjustment mechanism is carried by the framework.

3. The apparatus of claim 1 wherein the at least one adjustment assembly includes an additional adjustment mechanism for moving the elongate pin laterally relative to the axis in a direction.

4. The apparatus of claim 3 wherein the additional adjustment mechanism is carried by the framework.

5. The apparatus of claim 3 wherein the at least one adjustment assembly includes a second additional adjustment mechanism for moving the elongate pin laterally relative to the axis in an additional direction perpendicular to the first-named direction.

6. The apparatus of claim 5 wherein the second additional adjustment mechanism is carried by the first fastening assembly.

7. The apparatus of claim 1, wherein the bone comprises a longitudinal axis and a periphery relative to the longitudinal axis, the framework having a length sufficient to extend around at least a portion of the periphery of the bone in an operational position spaced radially from the bone.

8. The apparatus of claim 1, wherein the first fastening assembly is carried by the first end portion of the framework.

9. The apparatus of claim 8, wherein the second fastening assembly is carried by the second end portion of the framework.

10. The apparatus of claim 1, wherein the first fastening assembly comprises a clamp assembly.

11. A medical apparatus assembly for treating a bone of a mammalian body extending along a longitudinal axis and having a periphery relative to the longitudinal axis and being segmented into at least first and second portions comprising a framework having first and second end portions and a size and shape for extending around at least a portion of the periphery of the bone in an operational position spaced radially from the bone, a first mechanical assembly coupled to the first end portion of the framework and adapted for coupling the first end portion to the first portion of the bone and a second mechanical assembly coupled to the second end portion of the framework and adapted for coupling the second end portion to the second portion of the bone and at least one adjustment assembly carried by at least one of the framework and the first and second mechanical assemblies for moving the second mechanical assembly relative to the first mechanical assembly so as to reposition the second portion of the bone relative to the first portion of the bone, wherein the second mechanical assembly includes a pin having a sharpened tip for penetrating the second portion of the bone and the pin extends along an axis and the second mechanical assembly includes an adjustment mechanism for moving the pin proximally and distally along the axis relative to the second end portion of the framework.

12. The apparatus assembly of claim 11 wherein the first mechanical assembly includes an outrigger.

13. The apparatus assembly of claim 12 wherein the outrigger includes a targeting jig.

14. The apparatus assembly of claim 13 wherein the first mechanical assembly includes a bone plate.

15. The apparatus of claim 11 wherein the second mechanical assembly includes an additional adjustment mechanism for moving the pin laterally relative to the axis in a direction.

16. The apparatus of claim 15 wherein the at least one adjustment assembly includes a second additional adjustment mechanism for moving the pin laterally relative to the axis in an additional direction perpendicular to the first-named direction.

17. The apparatus of claim 11 wherein the at least one adjustment assembly includes a plurality of adjustment mechanisms for moving the second mechanical assembly in three orthogonal directions relative to the first mechanical assembly.

18. The apparatus of claim 11, wherein the first mechanical assembly comprises a clamp assembly.

19. A method for repositioning first and second portions of a segmented bone of a mammalian body with a medical apparatus assembly having first and second end portions and a central portion comprising introducing at least part of the first end portion of the medical apparatus assembly into the body, fastening the first end portion to the first portion of the bone, introducing at least part of the second end portion of the medical apparatus assembly into the body, fastening the second end portion to the second portion of the bone and manipulating the central portion of the medical apparatus assembly disposed outside of the body to move the second end portion relative to the first end portion so as to reposition the second portion of the bone relative to the first portion of the bone including moving the second end portion in first, second and third orthogonal directions relative to the first end portion.

20. The method of claim 19 wherein the second end portion of the medical apparatus assembly includes a pin for fastening to the second portion of the bone.

21. The method of claim 19 wherein the first end portion of the medical apparatus assembly includes an outrigger.

22. The method of claim 21 wherein the outrigger includes a bone plate.

23. The method of claim 22 wherein the first end portion of the medical apparatus assembly includes a targeting jig coupleable to the bone plate.

24. The method of claim 23, wherein the medical apparatus assembly includes a framework and the first end portion of the medical apparatus assembly includes a clamp assembly for attaching the framework to the targeting jig.

25. The method of claim 23 wherein the central portion and second end portion of the medical apparatus assembly are part of a first medical apparatus and for use with a second medical apparatus having a central portion and a second end portion, further comprising coupling the central portion of the second medical apparatus to the targeting jig, introducing at least part of the second end portion of the second medical apparatus into the body, fastening the second end portion of the second medical apparatus to the second portion of the bone and manipulating the central portion of the second medical apparatus disposed outside of the body to rotate the second portion of the bone about the second end portion of the first medical apparatus.

26. The method of claim 23 wherein the fractured bone has a third portion and for use with a second medical apparatus having a central portion and a second end portion, further comprising coupling the central portion of the second medical apparatus to the targeting jig, introducing at least part of the second end portion of the second medical apparatus into the body, fastening the second end portion of the second medical apparatus to the third portion of the bone and manipulating the central portion of the second medical apparatus disposed outside of the body to move the second end portion of the second medical apparatus relative to the first end portion of the second medical apparatus so as to reposition the third portion of the bone relative to the first portion of the bone.

27. The method of claim 19 wherein the second end portion of the medical apparatus assembly includes a pin having a sharpened tip for penetrating the second portion of the bone.

28. The method of claim 27 further comprising rotating the second portion of the bone about the pin.

29. The method of claim 19, wherein the medical apparatus assembly includes first, second and third adjustment mechanisms for respectively moving the second end portion in the first, second and third orthogonal directions and wherein the manipulating step includes manipulating at least one of a first, second and third adjustment mechanisms.

* * * * *